United States Patent
Pfenniger et al.

(10) Patent No.: US 10,282,976 B2
(45) Date of Patent: May 7, 2019

(54) ELECTRICALLY OPERATED HAND-HELD DEVICE FOR BODY CARE

(71) Applicant: TRISA HOLDING AG, Triengen (CH)

(72) Inventors: Philipp Pfenniger, Triengen (CH); Hanspeter Meier, Langenthal (CH)

(73) Assignee: TRISA HOLDING AG, Triengen (CH)

( * ) Notice: Subject to any disclaimer, the term of this patent is extended or adjusted under 35 U.S.C. 154(b) by 136 days.

(21) Appl. No.: 15/032,854

(22) PCT Filed: Apr. 17, 2014

(86) PCT No.: PCT/CH2014/000051
§ 371 (c)(1),
(2) Date: Apr. 28, 2016

(87) PCT Pub. No.: WO2015/061916
PCT Pub. Date: May 7, 2015

(65) Prior Publication Data
US 2016/0284208 A1   Sep. 29, 2016

(30) Foreign Application Priority Data

Oct. 30, 2013 (EP) .................................... 13405124

(51) Int. Cl.
*G08C 17/02* (2006.01)
*A61C 17/22* (2006.01)
(Continued)

(52) U.S. Cl.
CPC ........... *G08C 17/02* (2013.01); *A45D 34/042* (2013.01); *A45D 40/262* (2013.01);
(Continued)

(58) Field of Classification Search
CPC combination set(s) only.
See application file for complete search history.

(56) References Cited

U.S. PATENT DOCUMENTS

2002/0133308 A1 * 9/2002 Lundell .................. A61C 17/22
702/122
2003/0113685 A1 * 6/2003 Plank ................... A61C 19/004
433/29
(Continued)

FOREIGN PATENT DOCUMENTS

DE    102007053985 A1 *  9/2002  ............ A61C 17/16
DE    102007020100 A1    10/2008
(Continued)

OTHER PUBLICATIONS

May 3, 2016 International Preliminary Report on Patentability issued in International Patent Application No. PCT/CH2014/000051.

(Continued)

*Primary Examiner* — Junpeng Chen
(74) *Attorney, Agent, or Firm* — Oliff PLC

(57) ABSTRACT

An electrical hand-held device for body treatment, having a treatment part for performing at least one electrically operated body treatment function, and having a handle body for holding the hand-held device. The hand-held device further includes an electronic component for controlling the at least one electrically operated body treatment function. The electronic component contains a data transmission module for wireless, bidirectional data transmission. The data transmission module includes a microcontroller, at least one memory for storing data, and an antenna, wherein the data transmission module is designed to produce, in a contact-free manner, at least some of the electrical energy which is required for operation of said data transmission module.

20 Claims, 6 Drawing Sheets

Figure 1:

(51) Int. Cl.
*A45D 34/04* (2006.01)
*A45D 40/26* (2006.01)
*A46B 11/00* (2006.01)
*A47K 7/04* (2006.01)
*A61C 17/34* (2006.01)

(52) U.S. Cl.
CPC .......... *A46B 11/0072* (2013.01); *A47K 7/043* (2013.01); *A61C 17/221* (2013.01); *A61C 17/224* (2013.01); *A61C 17/3481* (2013.01)

(56) References Cited

U.S. PATENT DOCUMENTS

| | | | |
|---|---|---|---|
| 2004/0130915 A1 | 7/2004 | Baarman | |
| 2005/0116683 A1* | 6/2005 | Cheng | H01F 3/02 320/108 |
| 2008/0064006 A1 | 3/2008 | Quan et al. | |
| 2008/0146887 A1* | 6/2008 | Rao | A46B 7/04 600/300 |
| 2010/0036535 A1* | 2/2010 | Feine | A61C 1/0061 700/282 |
| 2011/0016648 A1* | 1/2011 | Kunita | A46B 15/0002 15/22.1 |
| 2011/0045778 A1 | 2/2011 | Stratmann et al. | |
| 2011/0098613 A1 | 4/2011 | Thomas et al. | |
| 2013/0214743 A1* | 8/2013 | Vorenkannp | H02J 17/00 320/155 |
| 2014/0266636 A1* | 9/2014 | Larsen | G08C 19/16 340/12.5 |
| 2014/0312702 A1 | 10/2014 | Uchida | |
| 2015/0293877 A1* | 10/2015 | Liang | A61B 1/00016 710/33 |
| 2016/0143718 A1* | 5/2016 | Serval | A46B 15/0022 15/22.1 |

FOREIGN PATENT DOCUMENTS

| | | |
|---|---|---|
| WO | 02/071970 A1 | 9/2002 |
| WO | 2006/105476 A2 | 10/2006 |
| WO | 2013/105279 A1 | 7/2013 |

OTHER PUBLICATIONS

Aug. 29, 2014 International Search Report issued in International Patent Application No. PCT/CH2014/000051.
Aug. 29, 2014 Written Opinion issued in International Patent Application No. PCT/CH2014/000051.

* cited by examiner

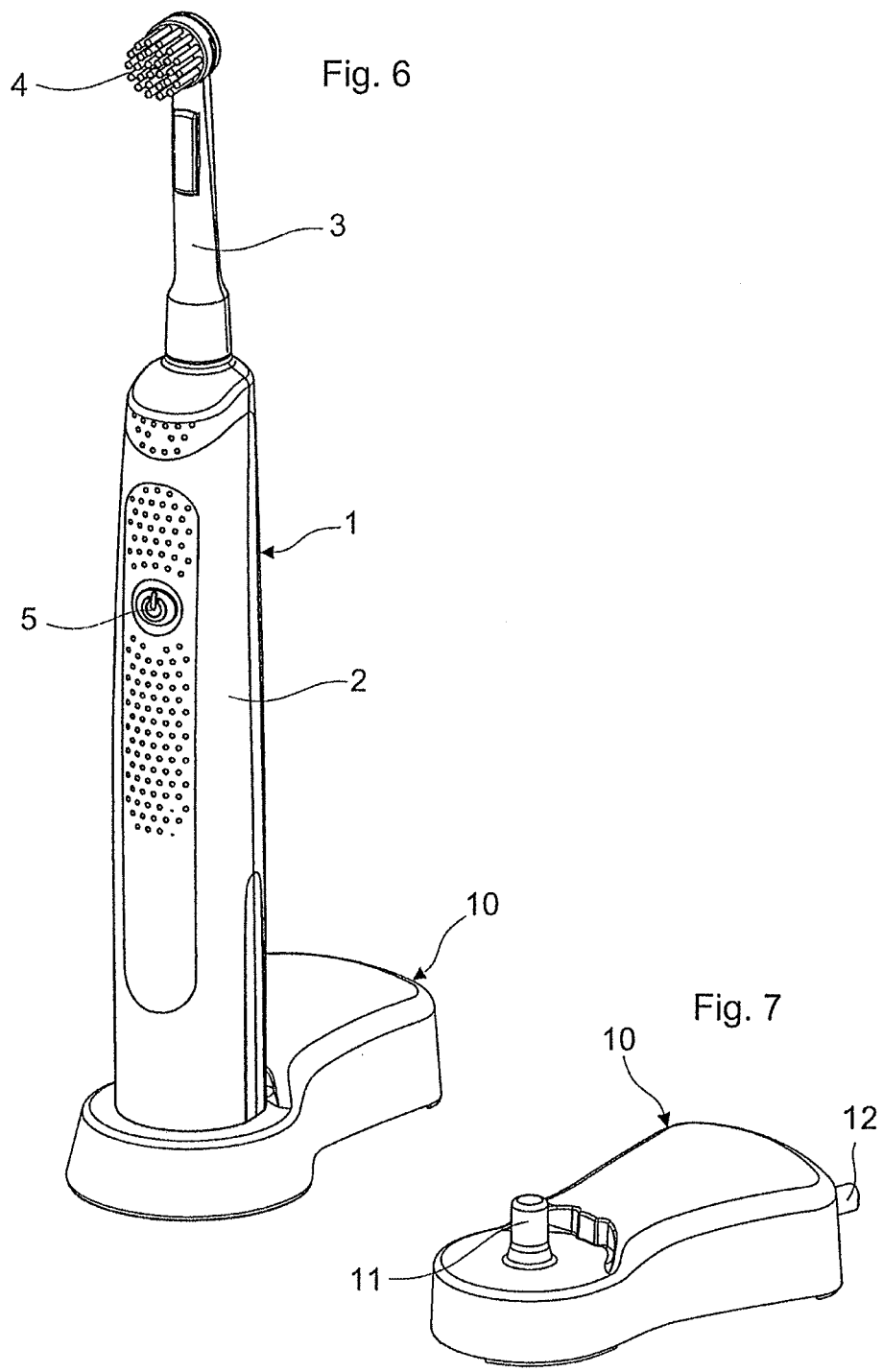

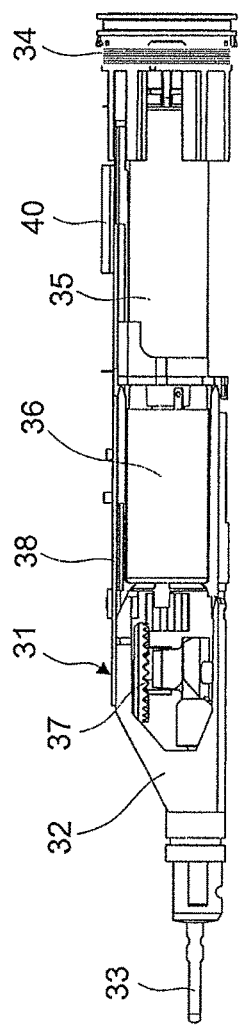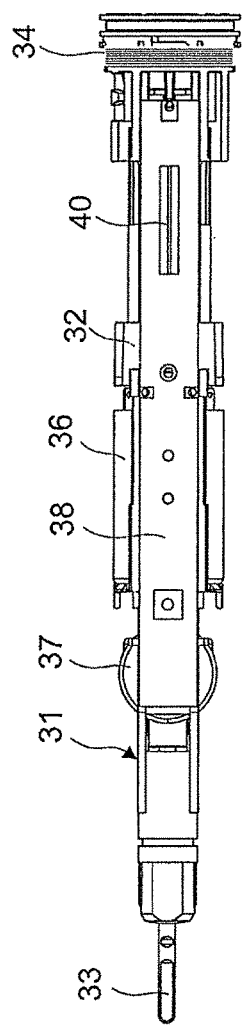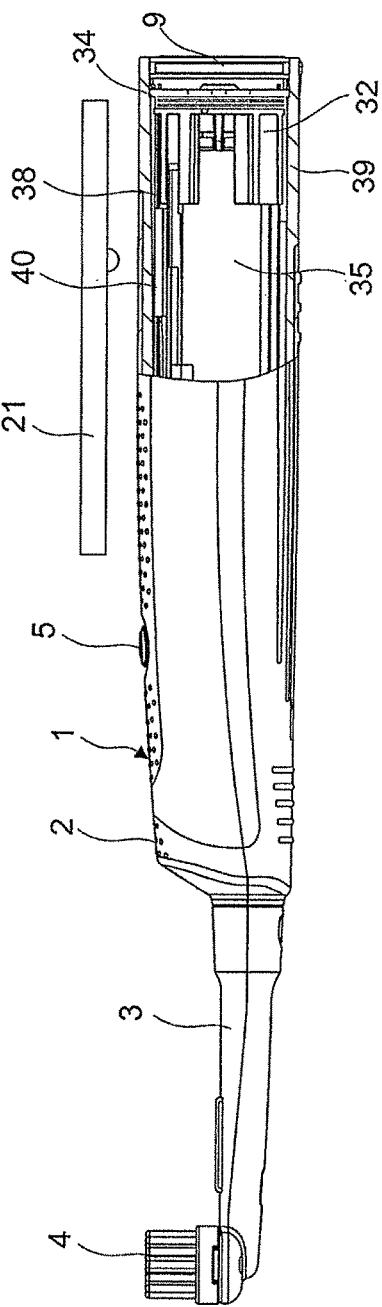

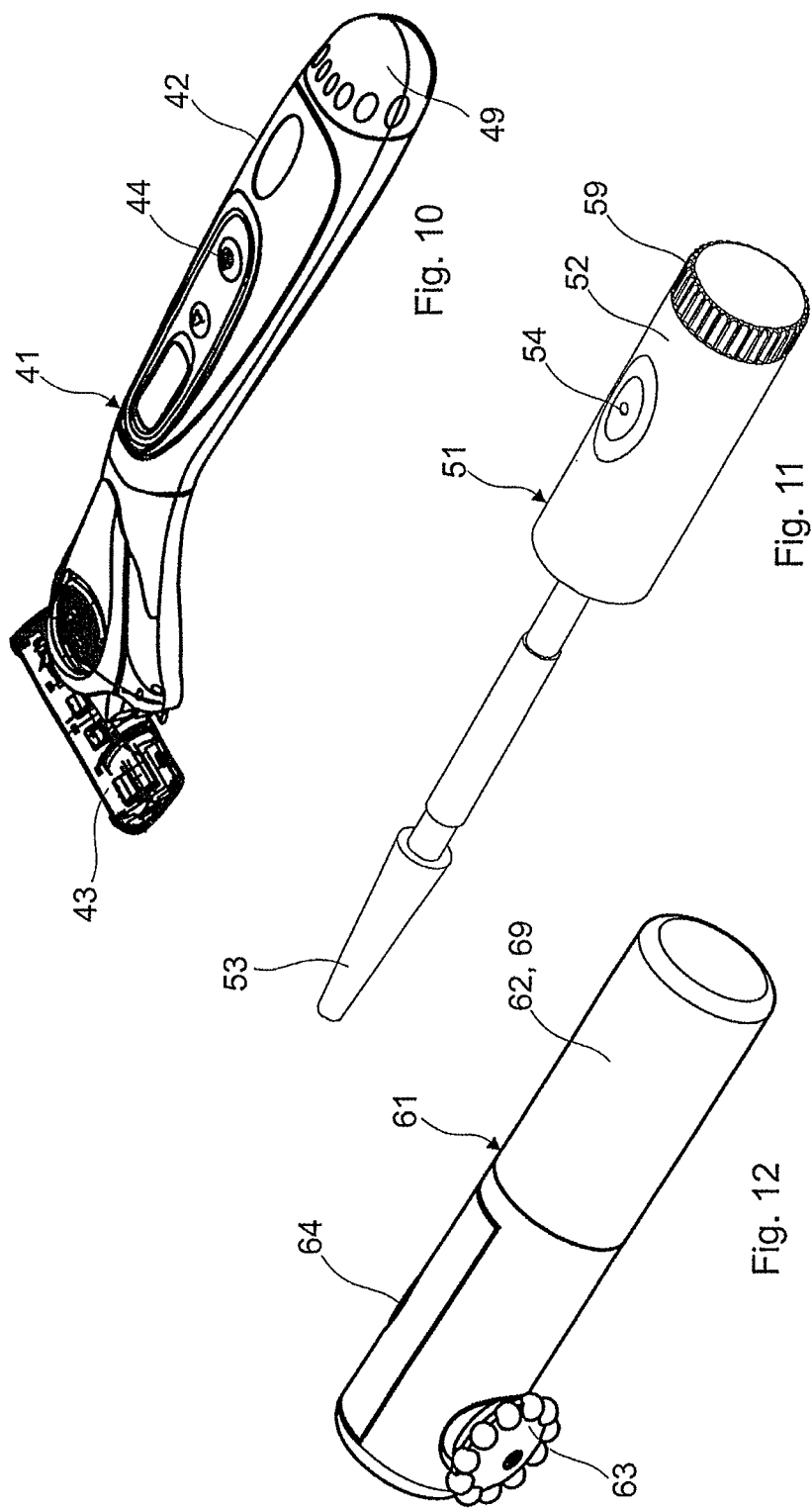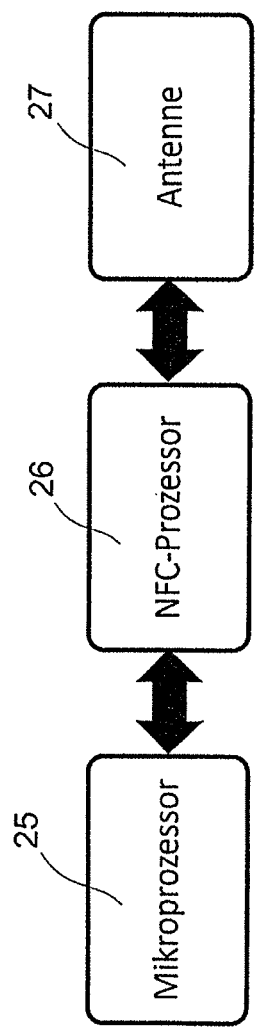

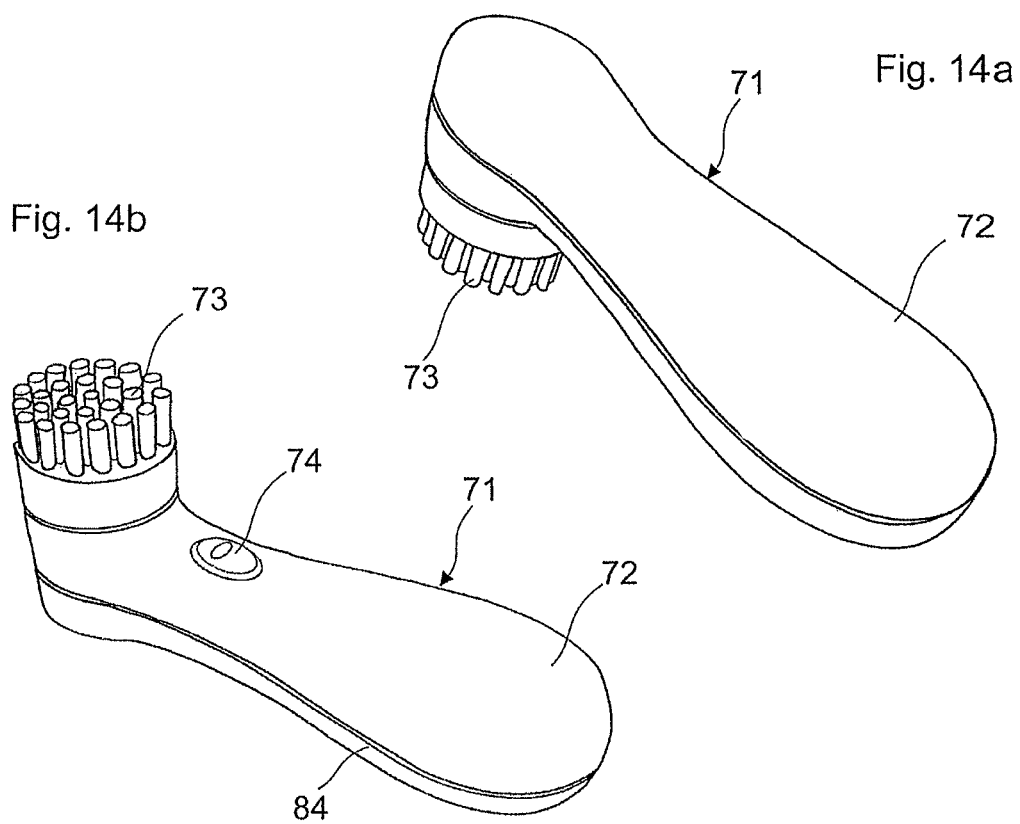
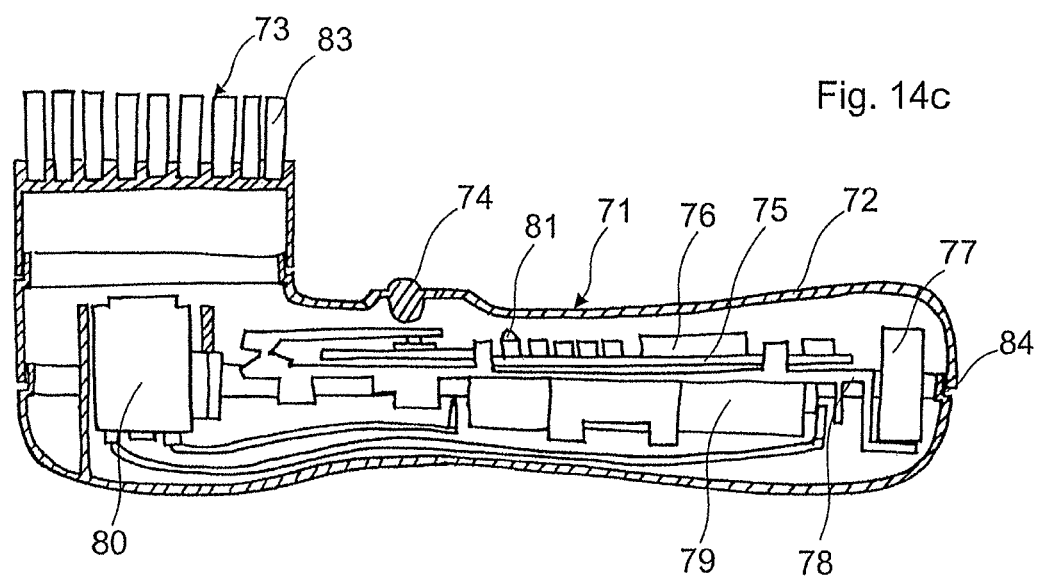

ELECTRICALLY OPERATED HAND-HELD DEVICE FOR BODY CARE

The invention concerns the field of body care. It relates to an electrical hand-held device for body care, with a care part for carrying out at least one electrically operated body care function and with a grip body for holding the hand-held device. The hand-held device moreover comprise an electronics part for the control of the at least one, electrically operated body care function.

A multitude of electrical hand-held devices are known for body care, and these permit the implementation of electrically operated body care functions. Thus for example electrical toothbrushes with which the brush head is set into motion via an electromotoric drive for implementing cleaning tasks are enjoying an increased popularity.

Concerning electrical toothbrushes, one differentiates between oscillating/rotating toothbrushes, oscillating/pivoting toothbrushes and sonic toothbrushes. An oscillating/rotating toothbrush is characterised by a round, rotating or oscillating brush head which oscillates about an axis perpendicular to the longitudinal axis of the hand-held device.

With oscillating/pivoting toothbrushes, the brush head executes a to-and-fro movement about the longitudinal axis of the hand-held device.

The teeth are mechanically cleaned by the bristles moving at a relatively high frequency.

With sonic toothbrushes, the brush head is set into oscillation. The oscillation frequency of the brush head however is greater than with a pivoting toothbrush. However, not only are the teeth mechanically cleaned, but also indirectly via a fluid in the mouth and which is set into oscillation by way of the toothbrush, which is in contrast to oscillating/pivoting toothbrushes.

Moreover, there is the possibility of setting the brush head into oscillation by way of vibrations. In this case, the motor e.g. has an eccentric which causes the vibrations.

Electrical toothbrushes can be differently complex, i.e. can be designed with more or less additional functions, irrespective of the functional principle. Thus the electric components of inexpensive models often merely comprise an energy cell in the form of a battery, an electromotorically operated drive as well as an on/off switch.

Electrical toothbrushes in higher price categories often yet comprise a microcontroller with a data memory for implementing further control functions which go beyond the mere switching-on and switching-off of the toothbrush. This for example can be the control of cleaning intervals, different cleaning powers or the detection and display of the charged status of an energy cell.

However, basically what is absent from conventional electrical toothbrushes and very generally from electrical hand-held devices for body care is the possibility of extensively and systematically collecting operating data and of evaluating this for monitoring and optimising the body care, in particular dental care.

Conventional hand-held devices, in particular electrical toothbrushes moreover comprise standard settings (e.g. care programs and parameters for example), which cannot be specifically adapted to the user or only within a very restricted scope. This is to say that the possibility of user-defined settings of e.g. operating parameters, control functions and care programs is absent with conventional hand-held devices.

Moreover, the possibility of acquiring and evaluating operating data as well as the possibility of inputting data specific to the user, for the purpose of optimising the body care function on the basis of evaluated operating data is also absent from the conventional hand-held devices.

This in the one hand is due to the fact that the functions described above render necessary the application of extended electronics. The additional electronics however are comparatively expensive and significantly increase the cost of the device. The increasing costs of the hand-held devices are additionally accentuated if the measures for the protection of the electronics on the hand-held devices and which are described hereinafter have yet to be implemented.

Moreover, limits are placed upon the application of complex electronics in hand-held devices for body care due to the limited size of these and thus the limited availability of space. This for example also relates to the installation of displays in the hand-held device. As a rule, only small displays can be incorporated into such hand-held devices, by way of which displays at best only numbers or letters can be represented, but graphic representations or larger blocks of information can only be represented in a greatly limited manner or not at all.

The environment, in which the hand-held devices are applied for body care, specifically the wet/humid regions, also places limits upon the use of complex electronics, or renders necessary special measures, e.g. sealing measures, with regard to the hand-held device. A further reason which appears to render to application of complex electronics in hand-held devices for body care more problematic, lies in the handling of the hand-held devices. These are subjected to knocks and impacts due to their use as hand-held devices. Particular measures for the protection of the electronics from knocks and impacts, e.g. on dropping would also be required here.

The published document DE 10 2007 020 100 A1 for example describes an electrical toothbrush with a transmitter, by way of which data can be transferred to an additional apparatus with a display device. The display device permits the display of the data. The functionality of the toothbrush is this restricted to the unidirectional transmission of data from the toothbrush to the additional apparatus.

It is now the object of the invention, to suggest an electrical hand-held device for body care and a functional unit with such an electrical hand-held device, which has an extended functionality and for example permits the acquisition, evaluation and representation of operating and sensor data. The hand-held device or the functional unit should moreover also permit the acquisition of user-specific data and the implementation of this in user-specific care programs or control functions for the control of the electrical hand-held device.

This object is achieved by the features of the independent claims 1 to 16. Special further developments and embodiments of the invention are to be deduced from the dependent claims, the description and the drawings.

The invention is thus characterised in that the electronics part comprises a data transmission module, preferably for the wireless, bidirectional data transmission. "Wireless" in this context means that no connection in the form of a physical data lead (e.g. wire, glass fibre) for the transmission of data from the transmitter to the receiver is necessary between the transmitter and receiver. The data transmission in contrast takes place via electromagnetic waves, in particular radio waves. Wireless therefore does not exclude two devices being able to or having to physically contact one another for the purpose of data transmission.

Other means for data transmission are likewise possible, e.g. a wire connection, e.g. via USB connection or microphone connection of the mobile device. A wireless connection is however given preference.

The hand-held device in particular can also comprise an electrical functional element for implementing the electrically operated body care function. The electrical functional element is explained in more detail further below.

The data transmission module comprises an electronics unit for the wireless, bidirectional transmission of data. The data transmission module can comprise the following elements:
a data transmission device with:
an antenna,
receiving means for receiving and demodulating data signals,
transmitting means for modulating and for transmitting data signals,
a microcontroller;
an in particular non-volatile memory for storing data;
as the case may be, a mechanical unit for the mechanical transmission of data.

The memory can be physically integrated into the microcontroller. Moreover, parts of the data transmission device can be physically integrated into the microcontroller.

The data transmission device in particular comprises a HF (high frequency) part. The antenna for example is a component of this HF part. In particular, the data signals to be transmitted are modulated or the incoming data signals are demodulated, in the HF part.

The microcontroller of the data transmission module in particular is a communication processor. This has the task of processing the wireless data traffic with an external mobile device. The task of the communication processor in particular can include the processing of data for transmitting and the processing of received data for further processing.

The microcontroller of the data transmission module can be integrated in the device processor of the hand-held device which is described in more detail hereinafter and which controls the functions of the hand-held device.

The data transmission module in particular can be designed to obtain at least a part of the electrical energy necessary for its drive, in a contact-free manner.

The data transmission module in particular can be designed to obtain all of the electrical energy necessary for its operation, in a contact-free manner.

"Contact-free" in this context means that no electrical contact for the transfer of electrical energy from an energy source to a consumer is created, in order for the consumer to be able to be operated. Contact-free therefore does not rule out two devices being able to or having to physically contact one another for the purpose of energy transfer.

In this case, it is the case of a passive data transmission module. The operation for example includes the data transmission. The operation can also comprise the processing of internal processes on the microcontroller.

The supply of the microcontroller of the data transmission module with electrical energy can be effected for example via an internal energy cell, in particular battery or a lead-connected electricity supply. The microcontroller in particular can be supplied with electrical energy via a lead connection by the subsequently described device processor.

The microcontroller of the data transmission module however can also obtain its energy for data processing in a contact-free manner, e.g. from the electromagnetic waves produced by the mobile device, which is to say from the respective electromagnetic field.

In particular, the transmitting means can obtain the energy for modulation and for transmitting data signals, in a contact-free manner, e.g. from the electromagnetic waves which are produced by the mobile device, which is to say from the respective electromagnetic field.

In particular, the receiving means can obtain the energy for receiving and for demodulation of data signals, in a contact-free manner, e.g. from the electromagnetic waves which are produced by the mobile device, which is to say from the respective electromagnetic field.

In particular, all electrical energy for carrying out the data transmission can be obtained in a contact-free manner.

The data transmission module in particular can be designed to obtain electrical energy in a contact-free manner via electromagnetic waves, such as radio waves, in the influence region of which the associated antenna lies. Such methods are also indicated as energy harvesting or ambient backscatter. The mentioned electromagnetic waves in particular are produced by the mobile device.

Moreover, it is also possible for the hand-held device to comprise a photovoltaic cell for converting light into electrical energy which is used for example for the operation of the microcontroller of the data transmission module and/or for the data transmission.

Moreover, it is also possible for the hand-held device to comprise a thermoelectric unit which operates according to the Seebeck effect and converts heat into electricity. Such a unit can be used for example for the operation of the microcontroller of the data transmission module and/or for the data transmission.

The data transmission module in particular can be designed for a data transmission according to the principle of near field communication NFC. One particular application of NFC is as an international transmission standard for the contact-free exchange of data by radio technology over short distances. The range (transmitting distance) can be limited to 20 cm, in particular to 10 cm. The transmitting distance is often even limited to a few centimeters, e.g. maximal 5 cm. The lower the range, the closer do the devices need to be held to one another for the purpose of communication. On the other hand, the danger of the communication being compromised due to interfering fields is also reduced.

The data transmission rate as a rule is comparatively small. It can e.g. reach maximally up to 424 kBit/s. The data transmission is effected according to the NFC standard at a frequency of 13.56 MHz.

Thereby, the antenna and the microcontroller of the data transmission module should be in resonance at 13.56 MHz, which due to the design of the data transmission module (NFC module) leads to an inductance of the antenna/coil of 4.7 microhenry.

A particular application of NFC technology is described by the standards ISO 15693 and -18000-3.

NFC permits the exchange of data between two devices which are briefly paired without a special logging in. Moreover, no errors occur when alternately assigning the pairs, since the devices must be held close to one another for this. The assignment of the paired devices with NFC is therefore effected by the user himself.

NFC technology is characterised by its rapid energy transmission, reduced antenna size and above all by the fields interfering to a lesser extent, in comparison to other radio techniques for the data exchange between two devices in the near field.

The data transmission however can also be effected via other, for example standardised radio technologies such as Bluetooth, in particular Bluetooth low energy (BLE), wireless personal area network (WPAN), e.g. ZigBee, WLAN, or Wife via WLAN. The data transmission can also be effected via infrared (IR).

With a data transmission based on WLAN, the hand-held device can comprise a drive for receiving memory cards with a Wi-Fi function, e.g. Eye-Fi cards. Eye-Fi cards are flash memory cards, such as SD (secure digital memory) or which is to say SDHC (SD high capacity) cards, with a Wi-Fi function, which permit the wireless transfer of data to the mobile device.

The user differentiation can be effected via different ones of memory cards when using such memory cards with a Wi-Fi function.

The respective associated communication protocols can be applied for the communication between the hand-held device and the mobile device. These can be the communication protocols which are usually used for Wi-Fi, NFC, Bluetooth, ZigBee, WLAN, BLE or WPAN. Proprietary communication protocols can likewise be applied. The standard is defined specifically by the manufacturer in this case.

It is also possible to apply communication protocols which are based on telefax, Morse, TCP/IP or USB.

It is also possible for the hand-held device and the mobile device to be able to communicate with one another via optical signals, e.g. in the visible range (by way of LED) or, as already mentioned, in the infrared range. The optical signals can be light pulses. Thus for example the duration of an optical signal, the number of transmitted optical signals and/or the intervals between the transmitted optical signals can comprise information.

The hand-held device via one or more LEDs for example can emit optical communication signals which are detected by a camera in the mobile device and which are interpreted or translated by the mobile device.

It is also possible for the hand-held device and the mobile device to be able to communicate with one another via acoustic signals, such as sounds. The receiver, e.g. the mobile device accordingly comprises a microphone. The sounds e.g. are characterised by different frequencies for example. Thus for example the duration of an acoustic signal, its frequency, the number of emitted signals and/or the intervals between the emitted acoustic signals can comprise information. Acoustic signals can assume a frequency in the non-audible range, e.g. ultrasound or infrasound, so that these do not act in an interfering manner.

The acoustic signals can thus e.g. be produced by the motor of the hand-held device. The frequency of the motor sound can be changed for example by way of varying the speed, from which a sequence of sounds (tones) of different frequency can be generated and this sequence contains the information. In particular, a whistling which can be used for the transmission can be produced in a quite targeted manner by the motor.

The actual data transmission can be based on the principle of amplitude modulation (ASK=amplitude shift keying) or on the principle of frequency modulation (FSK=frequency shift keying) with the transmission of signals (amongst other things, optically or acoustically). Thereby, a magnitude/ characteristic of the transmission medium is adapted or changed in each case, and this change in turn can be converted into a piece of information by way of decoding.

A wired communication between the mobile device and the hand-held device can moreover also be envisaged. Thus e.g. the audio interface, a USB interface or a proprietary data interface of the manufacturer on the mobile device can be used for a wired communication with the hand-held device. The hand-held device in this case likewise comprises a suitable interface, such as e.g. a micro-USB interface (standard interface) or a lightning interface (proprietary interface of Apple).

The data transmission or transfer between the mobile device and the hand-held device can be achieved by inductive or capacitive means.

The data transmission to the mobile device can also be carried out in a mechanical manner. In this case, the mobile device or a mechanical unit connected to the mobile device comprises means in order carry out a mechanical movement.

The hand-held device in this case moreover comprises an interface for receiving this mechanical movement. With regard to this receiver, it is preferably the case of a switch. With regard to this, it is there preferably the case of the on/off switch of the hand-held device or a switch for changing the operating condition of the hand-held device. Data can be transferred to the hand-held device by way of a certain sequence of the mechanical movement of the mobile device, in order with this, to change operating parameters, control data, user data or care programs. The microcontroller of the data transmission module and the device processor of the hand-held device in particular are identical in the case of a mechanical transmission.

Within the framework of the invention, it is also possible for a bidirectional data exchange between the hand-held device and the mobile device not to be effected by way of the same transmission technologies. Thereby, all data transmission technologies which are specified in this document can be combined with one another.

EXAMPLES hand-held device communicates optically (e.g. LED)— mobile device communicates mechanically;
hand-held device communicates acoustically (e.g. sound)—mobile device communicates mechanically;
hand-held device communicates acoustically (e.g. sound)—mobile device communicates electromagnetically;
hand-held device communicates optically (e.g. LED)— mobile device communicates electromagnetically.

The data transmission module in particular comprises a non-volatile memory. The non-volatile memory can e.g. be divided into two regions. A first e.g. larger region is used for storing acquired or detected data such as operating data, readings, operating parameters, or control data, care programs or user data. A second, e.g. smaller region is used for storing the operating parameters of the data transmission module or of the associated microcontroller.

The operating parameters, control data, user data or care programs can be transferred from the mobile device to the hand-held device, as is described further below.

The hand-held device is in particular is designed for the exchange of data with an electronic mobile device in a bidirectional and preferably wireless manner, via the data transmission module.

The electronics part of the hand-held device can moreover comprise a microcontroller for the processing of data and for the control or regulation of the electronic body care functions, hereinafter called device processor. The data e.g. is operating data, sensor data, control data or user data.

The device processor is connected to the microcontroller of the data transmission module via one or more communication leads, for the purpose of data transmission to a mobile device. These e.g. are designed as strip conductors on a circuit board.

In an embodiment, the device processor and the microcontroller of the data transmission module do not communicate during operation of the hand-held device. These preferably communicate directly after operation of the hand-held device or after a certain time delay, e.g. after a few seconds to minutes.

The device processor can fetch certain parameters from the memory of the microcontroller of the data transmission module by way of the communication lead or leads, for the operation of the hand-held device. Thereby, the memory positions are clearly fixed in the memory of the microcontroller and also stored in the device processor accordingly.

The device processor can comprise a non-volatile program memory. The operating software for the device processor is stored in the program memory for example. The program memory can e.g. be a flash memory, such as a flash EEPROM.

The memory can be written, so that certain parameters can be changed in the memory, for example variables which can be changed by the user. Moreover, in particular standard values are stored in the device processor, and these permit the recharged hand-held device to also be taken into operation after the energy cell has been completely emptied and the user-defined memory values have therefore been lost.

The device processor can comprise a volatile random access memory (RAM). This can be provided for storing temporary data. Such temporary data can e.g. be operating parameters which change during operation, e.g. a timer for a use or a zone timer for various zones of use of the hand-held device for body care. With a toothbrush for example, this can be a quadrant timer for the quadrants of a set of teeth.

With regard to a facial care device, this e.g. can be a 3-zone timer for the two cheeks and the forehead. Such a memory is characterised by short access times compared to non-volatile memories.

The device processor can comprise a non-volatile writable and readable (permanent) data memory, e.g. an EEPROM. This e.g. serves for storing operating data and sensor data, operating parameters as well as control data. The non-volatile data memory can thus comprise standard values or default values for the operation of the hand-held device.

The microcontroller of the data transmission module can be designed so that this can communicate at a time via only one interface, i.e. not simultaneously via several interfaces. The communication connection to the device processor can thus lead via a first interface. The first interface for example can be a serial data bus, such as a I²C interface (inter-integrated circuit). The communication connection to the HF part or to the antenna can lead via a second interface.

This means that the microcontroller of the data transmission module cannot simultaneously communicate with the device processor on sending or receiving data. Accordingly, no data can be transferred from the microcontroller of the data transmission module to the device processor and vice versa, during a preferably wireless data transmission.

Moreover, the microcontroller of the data transmission module cannot receive or send data when this communicates with the device processor. No data can be received or sent during the operation, since operating data and/or sensor data is continuously transferred from the device processor to the non-volatile memory of the data transmission module during operation of the hand-held device.

For this reason, the hand-held device in particular is designed such that the communication between the mobile device and the hand-held device can only take place when the hand-held device is not in operation. This means that a communication between the mobile device and the hand-held device is not possible when the hand-held device is in operation. "In operation" means that the or an electrical functional element is activated.

The hand-held device on the other hand cannot be put into operation, i.e. the or an electrical functional element cannot be activated, when the mobile device and the hand-held device communicate with one another.

The microcontroller of the data transmission module can e.g. be designed to put the device processor into a condition, e.g. by way of deactivation, in which the communication with a mobile device is possible, for the purpose of building up a communication connection with the mobile device.

The build-up of the communication between the data transmission module and the device processor is therefore usefully configured such that the data transmission module in each case can only communicate via one interface, since otherwise the possibility of data being corrupted exists. This for example can lead to the user application data not being correct or to the operating parameters of the hand-held device being incorrectly set and the device not longer being capable of operation of account of this.

Alternatively, it is possible for the communication with the mobile device to also be able to take place when the hand-held device is in operation. Thus a real-time transfer of data is possible at least with certain communication technologies, such as e.g. Bluetooth, in particular Bluetooth low energy (BLE), wireless personal area network (WPAN), e.g. ZigBee, WLAN or Wi-Fi via WLan.

One can envisage data from the device processor for example being stored beforehand in the non-volatile, i.e. permanent memory of the data transmission module, for transmission to the mobile device and being read out again from this memory for the purpose of a wireless transmission to a mobile device. Thus data such as operating data and sensor data which is to be transferred to the mobile device, e.g. before its transfer can be transferred from the device processor to the data transmission module and be written onto the permanent memory of the data transmission module. This is effected for example during the operation of the hand-held device or at the end of the operation.

Data which the data transmission module receives e.g. from the mobile device, is e.g. stored in the permanent memory of the data transmission module. The data can be read out again from the permanent memory and be transferred to the device processor for further use.

The permanent memory of the data transmission module amongst other things can therefore serve as intermediate memory, in order to thus permit the alternating communication of the microcontroller of the data transmission module with an external mobile device and the internal device processor.

The communication with the external mobile device for example permits only the exchange of data which is stored in the memory of the data transmission module. Any data which is exchanged must be stored beforehand in the memory of the data transmission module.

Further details concerning the functionality between the hand-held device and the mobile device are to be deduced further below in the context of the functional unit of the hand-held device and the mobile device, which is likewise claimed.

The antenna can be connected to the microcontroller of the data transmission module in a direct manner. The device processor and the microcontroller can be arranged on a common circuit board, also called board. The antenna of the data transmission module can likewise be arranged on the common circuit board. The permanent memory of the device processor and/or of the microcontroller or of the data transmission module can likewise be arranged on the common circuit board. The circuit board with the mentioned components can be part of an assembly unit which is described in more detail further below.

The microcontroller of the data transmission module and the device processor can form a unit and in particular be arranged on a common circuit board.

The antenna can be arranged such that the conductor circuits are not closed until after the assembly in the device housing has been effected. This is effected for example by way of suitably designed contact elements. The contact elements in the hand-held device can e.g. be designed and arranged such that these ensure a reliable contacting.

The antenna can comprise a coil with a plurality of windings of copper wire. The coil can comprise 10 to 30 windings, preferably 15 to 20 windings.

The number of windings is preferably adapted such that the specified resonant frequency is achieved. This is dependent on the inductance and the current. The inductance of the antenna/coil in the case of NFC application is 4.7 microhenry and results from the number of windings and from the material characteristics of the ferrite core.

The copper wire can have a diameter of 0.2 to 1.2 mm, preferably 0.4 to 1 mm.

The antenna can comprise a coil core or ferrite core with a length of 10 to 40 mm, preferably 15 to 25 mm.

The antenna can comprise a coil core, or a ferrite core, with a diameter of 1 to 8 mm, preferably 2 to 4 mm.

The design of a ferrite antenna is selected such that this lies as closely as possible to the resonant frequency.

The electrical characteristics of the antenna in particular are matched to the processor, in particular to the NFC processor.

The electronics part of the hand-held device can moreover comprise an energy cell such as a battery for the supply of the device processor as well as of the electrical functional element with electricity.

The term "battery" according to definition includes primary cells as well as the preferred secondary cells and is basically also to be equated with the term energy cell.

The hand-held device e.g. comprises a re-closable receiving chamber for receiving the energy cell, in particular the battery.

The secondary cell, also called accumulator, as well as the hand-held device can be designed such that the accumulator can be taken from the hand-held device which is to say from the receiving chamber and re-inserted again, for charging on an external charging device, also called charging station.

Primary cells can also be inserted into the hand-held device which is to say into the receiving chamber and removed from this again, in the same manner. This however is effected with the difference that the primary cells are merely exchanged.

The accumulator can also be installed in the hand-held device in a fixed manner. "Installed in a fixed manner" means that the accumulator does not need to be removed from the hand-held device for charging. In this case, the charging of the accumulator is preferably effected by way of a contact-free energy transmission. The contact-free energy transmission in particular is an inductive energy transmission. In this case, the hand-held device, in particular the grip body comprises an induction coil which is connected to the secondary cell. The secondary cell can be charged in a contact-free manner on an external charging device without removal from the hand-held device in this manner. The hand-held device is brought to the charging device for this. The charging device which for example is designed as a charging station can comprise an insert receiver, into which the hand-held device can be inserted whilst forming, e.g. loose insert connection.

The electrical functional element of the hand-held device can be:
  an electromotoric drive for the mechanical movement of a body care element. The mechanical movement in particular can be a rotation, an oscillation, a pivoting or a vibration;
  a pump for delivering a fluid such as a liquid or gas. The pump for example can be for delivering a fluid such as water or a water-containing liquid, for an oral irrigator. The pump can also serve for delivery of a liquid toothpaste or also mouthwash. The pump can moreover serve for atomising a care fluid;
  a cutting device for cutting, in particular shaving or trimming, hair, e.g. beard hair. The cutting device e.g. can comprise a razor blade;
  a device for plucking hairs for hair removal;
  an ionising device for producing a current flow in the body or on the skin of the user by way of ionising;
  an ultrasound device for ultrasound diagnostics;
  a device for producing light, e.g. UV (ultraviolet) light. This for example can serve for the disinfection of body care elements such as brushes;
  an electrical heating for heating a body care element;
  an electrical cooling device for cooling a body care element.

The electrical functional element can also have two or more than two of the functions mentioned above.

The hand-held device can moreover also comprise one or more electrical functional elements, in particular of those mentioned above, and the associated functionality. The electrical functional elements which are mentioned above by way of example can also be infinitely combined with one another with regard to this.

The grip body and the care part can be designed in a separate manner and be connectable to one another. The care part of example can be stuck or snapped onto the grip body. The grip body and the care part can also be designed as one piece.

The care body element is a constituent of the care part and can be a brush or a brush head, a massage element or massage head, a nozzle head, a fluid dispensing unit or razor blade or blade head. The body care element can be a releasable or integral part of the care part.

The grip body can comprise a housing which forms a receiving space. The housing in particular is of plastic. The housing can therefore be manufactured with the injection moulding method.

The housing e.g. can be manufactured by way of a multi-component injection moulding method. The housing wall in particular can be constructed in a multi-layered, e.g. two-layered or three-layered manner. The housing can thus be manufactured in two or more injection moulding steps. The housing can be manufactured of one or more different plastics. The multi-layered housing wall can therefore be manufactured of one or more different plastics. The multi-layering e.g. can be regional and does not need to be given on all regions of the housing.

It is moreover possible to manufacture the housing of several, in particular of at least two shell-like housing parts. The individual shells for example are again manufactured with the multi-component injection moulding method. The connection of the shells can be effected by way of the common connection technologies, for example by way of peripheral injection with the injection moulding method, bonding, welding, e.g. ultrasound welding.

In particular, with the described shell-like construction of the housing, it is possible for a closure cover for the device to be superfluous, since the construction of the device is such that the receiving space is closed off on connecting the shells. The closure is thereby produced by the shell-like housing parts and, at the most, also by way of further elements which are arranged on the connection lines/connection surfaces or in recesses in the shells.

The housing of the grip body can be designed in a hollow-cylindrical manner. The receiving space can be closed by a closure cover, at that end of the housing which is arranged opposite to the care part. The receiving space of the housing can be closed via a screw connection or bayonet connection, by way of a closure cover. The closure cover can e.g. be a screw cap.

That end of the housing, to which the care part connects, can likewise be open. This housing opening for example can be closed off via elements of a carrier structure which projects through the housing opening. Seals on the carrier structure can additionally seal off the housing.

Housings of the type described above can be applied with all mentioned hand-held devices for body care.

One or more of the following components in particular can be arranged in the receiving space of the housing:
  the electronics part, e.g. with the device processor and microcontroller of the data transmission module;
  one or more electrical functional elements or parts thereof, and associated mechanical components;
  the energy cell;
  if provided: sensors for detecting readings;
  if provided: the induction coil.

The induction coil in particular is arranged at that end of the housing which is opposite to the care part, and in particular close to the closure opening if this is present.

The components which are mentioned above e.g. can be inserted through a closure opening which can be closed for example by the closure cover. The closure opening thus forms a push-in (insert) opening, e.g. for an assembly unit. The closure opening can therefore be used for the assembly as well as for a later repair or also for disassembly.

If the housing is constructed from several shell-like housing parts, as described above, then the assembly of the mentioned components e.g. in one or more shells can take place before these are connected to one another.

The electronics unit together with the electrical functional element can be designed as an assembly unit. If the accumulator is installed in the housing in a fixed manner, then the accumulator can also be part of the assembly unit. If the energy transmission for charging the accumulator is effected inductively, then the associated induction coil can also be part of the assembly unit.

The mentioned components of the assembly unit can be assembled on a carrier structure. The carrier structure can be of plastic. The carrier structure can be of one or more parts.

If the assembly unit is inserted through the closure opening into the housing, then this is designed as a push-in unit (insert unit), also called push-in module.

The assembly unit can be designed as an inlay unit which is laid into the housing, with the construction of the device by way of the mentioned shell-like housing parts.

According to a particular embodiment variant, the hand-held device comprises an electromotoric drive for carrying out an electrically operated body care function. The electromotoric drive is controlled by the device processor.

The electromotoric drive in particular can be a brush motor, a brushless motor, a piezo motor or an oscillating armature motor.

The electromotoric drive has a certain motor speed. This indicates at which speed the motor shaft of the electromotoric drive rotates at its output. The speed which is available for the care part or for the body care element is assigned directly to this motor speed, after having run through gear stages and/or gear ratios as the case may be. The speed is hereinafter called application speed. The application speed corresponds to the speed of a mechanical movement of the body care element. This e.g. can be a rotation, an oscillation, a pivoting or a vibration. The application speed with a toothbrush e.g. can be the cleaning speed.

The switch for activating the hand-held device in particular can be a mechanical switch (mechanical push key, flip switch, etc.), a piezo-switch, a capacitive switch or also an optical switch.

The electromotoric drive and the antenna of the data transmission module can be arranged in the grip body. The electromotoric drive and the antenna for example are arranged at a distance of at least 2 cm to another. The magnet of the electromotoric drive exerts no interfering influence upon the antenna on account of this.

One additionally succeeds in the mobile device not coming too close to a magnetic source on account of the spacing of the motor from the antenna. The risk of the magnetic source for example deleting the memory in the mobile device or of parameters of the mobile device being reprogrammed by the magnetic field, are reduced by way of this.

The antenna can be arranged radially around the energy cell, and this energy cell can likewise be arranged in the grip body. The antenna and energy cell can have a distance of 1 mm or more to one another. An insulation, in particular an air insulation can be present between the antenna and the housing.

An arcuate antenna which for example is arranged at least partly around the energy cell can be attached radially to the energy cell in the arrangement.

The electromotoric drive in particular can be arranged in an upper section of the grip body which faces the care part. The antenna of the data transmission module in particular is arranged in a middle or lower section of the grip body which is away from the care part.

The antenna can be a ferrite antenna for the purpose of achieving high field strengths. The coil core in particular is aligned in the longitudinal direction of the hand-held device. The coil core can also be aligned perpendicularly or obliquely to the longitudinal direction of the hand-held device. The antenna can also be designed as an air coil without a ferrite core. The antenna can be aligned coaxially to the energy cell or to the electromotoric drive.

The antenna can also be a part of the induction coil for charging the energy cell, i.e. the secondary cell.

The antenna can also be designed in an extensively shaped manner. The antenna or its electrically conductive parts can be present e.g. in foil form. A foil-like antenna can be placed in the housing of the hand-held device in a shape which is not plane, e.g. arcuate.

The antenna can be label-like or be designed as a label. The antenna in particular can be designed as an NFC tag. The foil shape or label shape in particular is suitable for placing into a recess. This recess can be provided in a housing of the hand-held device, in particular of the grip body.

The antenna can comprise windings. The antenna can also be linearly constructed.

The antenna can e.g. be constructed from strip conductors which are arranged on a circuit board. The antenna can also be assembled on the circuit board. Thereby, it can be the case of the same circuit board, on which the microcontroller of the data transmission module is also located.

The antenna can be assembled on the circuit board as a so-called SMD component (surface-mounted device). The antenna can e.g. also be a patch antenna or PIF antenna.

The antenna can be fastened on one of the following components of the hand-held device via a material fit, non-positive fit and/or positive fit:
  on the housing, in particular on the housing of the grip body;
  on the closure cover;
  on an assembly unit, as described further above;
  on the carrier structure of an assembly unit, as described further above.

The material fit connection can be a bonding connection or be created by way of a moulding in plastic.

The housing can be transparent in the region of the antenna. The housing for example can comprise a viewing window. The user can visually localise the position of the antenna on the hand-held device by way of this. This permits him to position the mobile device as optimally as possible for data transfer.

It is also possible to render the position of the antenna visually visible by way of illumination which is visible from the outside. The illumination can be integrated in the housing or in the receiving space of the hosing. This can be effected independently of the presence of a viewing window.

Moreover, visually or tactilely perceivable symbols for localising the antenna can also be arranged outside on the surface of the housing. This can be effected for example by way of an injection moulding, a printing or a laminating of the housing. With regard to the symbol, it can be the case e.g. of an NFC symbol.

With this, the user recognises the position of the antenna for the optimal positioning of the mobile device with respect to the hand-held device, for data transmission. This is of significance concerning the application of NFC technology with a short range. Thus e.g. one or more LEDs on the hand-held device can illuminate or the electromotoric drive can switch on briefly (e.g. less than one second), in order to indicate the creation of the wireless connection.

Moreover, one can also envisage the mobile device or the hand-held device emitting a signal on reaching an optimal position of the mobile device with respect to the hand-held device. The signal can be perceived acoustically, visually or in a tactile manner. The user can subsequently start the data transmission by way of the mobile device.

The antenna, as mentioned, e.g. can be arranged in the region of the housing of the hand-held device, in particular of the grip body. An extensively-shaped antenna can be arcuate, e.g. rolled, for the purpose of adaptation to the housing shape or the spatial conditions in the housing. An extensive antenna however if possible is not arcuate or only to a small extent, in order to ensure an adequately high antenna power.

The antenna of the data transmission module which for example is designed in an extensively shaped manner can have one of the following arrangements:
  an arrangement directly on the inner side of the housing wall;
  an arrangement directly on the outer side of the housing wall;
  an arrangement between two layers of a housing wall which is constructed in a multi-layered manner;
  an arrangement integrated into the housing wall.

The housing in the region of the antenna can be designed with a thinner wall than in the remaining regions. The housing at least in the region of the antenna in particular consists of a non-conductive material such as plastic. The housing in particular also comprises no conductive components, at least not in the region of the antenna, so that the field is not subjected to interference. Interfering elements for example can be filets which are bonded onto the housing or embossed metal foils.

Moreover, it is possible to design the housing in the region of the antenna from a material which has characteristics for communication which are better compared to the material which is applied in other regions of the housing.

The antenna for example as an inlay part can be peripherally injected with plastic by way of an injection moulding step during the manufacture of the grip body or housing, and thus integrated into the housing wall of the grip body. The antenna can also be integrated in the closure cover in the same manner.

Moreover, it is also possible for the antenna to be assembled separately. Thus the antenna can be assembled into a deepening or recess in the inner wall of the housing, in particular of the housing of the grip body, or of the closure cover. The deepening or recess can be closed in a permanent or reclosable manner, by the cover. The antenna can also be moulded or bonded into the recess. The moulding or casting mass can be a plastic or an adhesive.

The antenna is preferably arranged as close as possible to the housing wall, so that the transmission through the housing wall is improved. The range of the field of the antenna outside the housing is larger due to the arrangement close to the housing wall.

A further positive point is achieved due to the arrangement of the antenna close to the housing wall. The antenna, seen from the housing wall, is not covered by other components in the housing.

The antenna is arranged in or on the housing, in particular in the housing of the grip body, preferably such that this antenna is directed to that side which, in the stable position of the hand-held device on a rest surface, does not face the rest surface, but the user. The antenna for example points towards the upper side of the toothbrush.

The antenna can lie on the side of the on/off switch. The antenna can lie in the proximity of the on/off switch. The antenna can lie on the side of a care head.

The hand-held device for body care according to the invention permits the application of a multitude of sensors for detecting readings, which e.g. provide information on the operation of the hand-held device, as is explained in more detail further below. The hand-held device can thus comprise one or more sensors for detecting one or more measured variables.

Thus e.g. a sensor can be provided for determining the pressing pressure, the position or location of the hand-held device, a temperature, the pulse or a pH value.

A biosensor e.g. for determining bacteria, plaque, odour or disease can moreover be provided.

An optical sensor can also be provided, e.g. for determining the cleaning performance or the surface nature.

A timer can moreover be provided for determining the duration of use.

Evaluations which provide the user with useful information, e.g. on the care behaviour, can be carried out with the determined data and readings. The evaluations can be statistical evaluations, such as determining average values, determining minimal and/or maximal values.

The determined readings can also serve for providing hints concerning the optimisation/improvement of the care behaviour. The parameters for the operation of the hand-held device can also be adapted to the individual user by way of the determined data and readings.

The evaluation of the data and readings can be possible e.g. in a set framework. This means that certain defined standard evaluations are possible. The evaluations for example can be made over certain periods of time which e.g. can be selected by the user.

The electrical hand-held device for body care can for example be an electrical oral hygiene device such as an electrical toothbrush, an electrical flosser, an electrical gum massaging device, an electrical interdental cleaner or an electrical oral irrigator.

The electrical hand-held device for body care for example can be an electrical wet shaver.

The electrical hand-held device for body care for example can be an electrical dry shaver.

The electrical hand-held device for body care for example can be an electrical cosmetics device, for example a mascara applicator such as mascara brush, or a nail varnish brush.

The electrical hand-held device for body care can for example be an electrical facial care device.

The electrical facial care device for example can be an electrical facial cleaning device.

The electrical facial care device for example can be a facial massage device.

The electrical facial care device can also be a combination of facial cleaning and facial massage device.

The electrical facial care device in particular can be an electrical facial brush.

The electrical hand-held device for body care for example can be an electrical body care device for the care of skin portions on the body. The body care device for example can be for the care of the feet, the legs, the arms, the tummy or the back.

The electrical body care device can be a body massage device

The electrical body care device can be a body cleaning device.

The electrical body care device can also be a combination of body cleaning and body massage device.

The care part of the electrical body care device e.g. can be a massage head and/or a cleaning head. The care part for example can be a brush head.

The care part of the facial care device can be a massage head and/or a cleaning head. The care part for example can be a brush head with a massage brush. A care cream can thus be massaged into the skin by way of the massage brush. The facial care device apart from the massage function can include a facial cleaning function.

The facial care device as also the body care device can be designed so that different care heads for different care steps can be stuck on. This e.g. can be a massage head with massage nubs or a brush head for massaging in a cream by way of a brush. The different care heads thereby have connection interfaces which are compatible with the care device.

The hand-held device, e.g. a toothbrush, a facial care device or a body care device can comprise one or more sensors for detecting operationally relevant readings. These for example can be the following sensors:

- a gyrosensor, accelerometer or acceleration sensor for measuring accelerations of the hand-held device;
- a position sensor for measuring the position or location of the hand-held device;
- a movement sensor for measuring the movement of the hand-held device;
- a pH sensor for measuring the pH value in the mouth region;
- a temperature sensor for measuring a body temperature or skin temperature;
- a humidity sensor for measuring the skin humidity or for measuring the humidity of the body care part or care head, in particular of the brush head;
- a mouth odour sensor;
- a pressure sensor for measuring the pressing pressure of the body care part or care head, e.g. upon the skin or upon the teeth;
- a pulse sensor for determining the pulse of the user;
- a blood pressure sensor for determining the blood pressure of the user;
- a proximity or contact sensor for determining when the contact from the body care part or care head to the teeth, to the skin or to another body part is created.

Of course, the respective sensors for determining measurement variables in the region of the mouth can be done away with, in the case that the hand-held device does not serve for oral hygiene.

According to a particular embodiment variant, the hand-held device is an electrical toothbrush. The electrical toothbrush comprises a grip body and a care part. The care part comprises a treatment head. The treatment head serves for the care and/or cleaning of the teeth. The treatment head for example is designed as a brush head. The care part in particular can be stuck on.

The toothbrush comprises a front side, also called upper side. The front side corresponds to that side of the toothbrush, to which the bristle field of the brush head is directed.

The toothbrush moreover comprises a rear side, also called lower side. The rear side is the side which is opposite to the front side which is to say the bristle field.

According a further particular embodiment variant, the hand-held device is a facial care device.

The facial care device comprises a grip body and a care part with a care head, also called treatment head. The treatment head can be designed for the massage of the face. The treatment head alternatively or additionally can be designed for cleaning the face. The treatment head can alternatively or additionally be designed for the care of the face, e.g. with a cream.

The treatment head for example can be designed as a brush head. According to this embodiment variant, the facial care device can be a facial brush.

The care part or the care head in particular is able to be stuck on.

The facial care device comprises a front side, also called upper side. The front side corresponds to that side of the facial care device, to which the treatment head or its parts acting upon the face are directed.

The facial care device moreover comprises a rear side also called lower side. The rear side is the side which is opposite the front side or the treatment head.

The facial care device comprises an electromotoric drive which interacts with the care head for producing a rotation movement and/or vibration movement in the care head. Vibrations can be produced via an eccentric element interacting with the electromotoric drive, and be transmitted onto the care head. The electromotoric drive can be arranged in the housing in the region of the care head.

A switch for switching the facial care device on and off can be provided in the grip body.

A circuit board can be arranged in the grip body. An NFC module with a transmitting and receiving unit can be arranged on the circuit board. An LED display for status displays can moreover be arranged on the circuit board.

Moreover, a secondary cell as well as an induction coil for charging the secondary cell can be arranged in the grip body. The secondary cell can be arranged in the longitudinal direction of the grip body. The induction coil can be arranged in the end of the grip body which lies opposite the care head.

The antenna can be arranged in the grip body. The antenna can be arranged on the circuit board. The antenna can be arranged in the longitudinal direction of the grip body, in particular parallel to the secondary cell. The antenna can thereby be arranged laterally to the secondary cell.

The antenna can moreover be arranged between the drive and the secondary cell. The antenna in this case can be orientated transversely to the longitudinal direction of the grip body.

The circuit board, the secondary cell, the antenna and the induction coil can be connected via a carrier structure or carrier component into an assembly unit.

The housing wall of the grip body can be divided in the longitudinal direction into two half-shells via a joining seam, by which means an access to the inside of the grip body and to the assembly unit can be created.

It is also possible for the grip body at its free end to be closable via a closure cover.

A charging station can be assigned to the facial care device as well as to the body care device, as already described at another place in this application.

The sensors which are mentioned in this document can be attached in the electronics part in the housing of the grip body, e.g. on the housing at the inside or outside, or on the care part, e.g. on the care head such as the brush head.

The sensors which are mentioned in this document, apart from the toothbrushes and facial care devices can also be applied in other hand-held devices, in as much as this makes sense or can be technically carried out, concerning the application purpose of the hand-held device.

If for example the pressure sensor measures a high pressing pressure of the care head, then this can be directly notified to the user, so that he reduces the pressing pressure during use. This notification can be effected optically (e.g. by way of LED), haptically (e.g. changing the motor power, interrupting the motor power), via a display or acoustically. On the other hand, the application speed of the care head can be reduced during use for compensation, on account of a measured, permanently too high pressing pressure. This is effected for example by way of reduction of the motor speed of the electric drive.

The accelerometer e.g. serves for determining impacts which act upon the hand-held device, e.g. by way of dropping. This information can be of relevance concerning guarantee claims.

With this, the spatial position and/or the movement course with the hand-held device can be additionally detected. This in turn provides information on the behavioural use of the hand-held device. Thus a brushing movement can be detected and thereupon one can evaluate as to whether this is quick or slow, is in small circles or linear or scrubbing. One can also determine as to whether all necessary zones have been cleaned (e.g. the facial zones with facial care devices, and e.g. quadrants of set of the teeth with toothbrushes).

An incorrect practise or a determined optimisation potential with the brushing movement or covering of the zones which is ascertained by way of this can be compensated by the setting of parameters in the hand-held device and/or mobile device. Thus for example the setting of a timer or a zone timer, an auto on-off function or the application speed of the care part can be adapted.

The invention moreover relates to a functional unit, comprising:
 a hand-held device for body care as described above, and
 an electronic mobile device, wherein the electronic mobile device comprises an active transmitting and receiving unit for the bidirectional, wireless data transmission between the hand-held device and the mobile device.

The bidirectional data transmission can be designed differently in each direction.

The functional unit quasi corresponds to a body care system with a hand-held device for body care and with a mobile device.

The electronic mobile device is preferably characterised in that this can be operated in a wireless manner with regard to the data transmission as well as with regard to the supply of electricity.

The charging procedure of the mobile device can however indeed be effected by way of a cable connection. The mobile device however preferably also has an energy cell for a wireless electricity supply.

Moreover, with regard to the mobile device it is preferably the case of a commercially available device. This means that the data processing processes and transfer processes or communications process which are according to the invention, in the context of the hand-held device in particular represent an auxiliary function of the mobile device.

The mobile device is preferably characterised by possible main functions, such as mobile telephoning (e.g. based on GSM (global system for mobile communications), SMS services, MMS services, and/or wireless internet access (e.g. via WLAN or GSM) whilst using a web browser.

The mobile device is further preferably also characterised in that this is operated with an operating system, which e.g. apart from a web browser also permits the use of software applications. The software applications can be downloaded for example from the internet via a web browser or via an App store. The App store is an internet sales portal for software applications, which is specific to the device.

The mobile device for example comprises a display for the display of information, a processor as well as a permanent data memory.

The active transmitting and receiving unit of the mobile device for transmitting and receiving data between the mobile device and the hand-held device can also be indicated as a transceiver. This is preferably designed for the active production of electromagnetic waves for the purpose of data transfer. The transceiver in particular is designed for NFC communication. The transmitting and receiving unit in particular can be an NFC module. This can be installed as standard in the mobile device for example.

The mobile device can e.g. be a mobile telephone, a smartphone, a tablet computer, a PDA (personal digital assistant), a notebook or a netbook.

The mobile device can also have a permanent, usable mains electricity supply.

The mobile device can have mechanical means for communication with the hand-held device. The mechanical means can comprise a key.

The mechanical means can e.g. be connectable to the mobile device e.g. via an interface on the mobile device, such as a microphone connection or USB interface.

These mechanical means can be coupled to the on/off switch of the hand-held device, in order to transfer information to the hand-held device.

Moreover, the mobile device can also be a so-called smartwatch. The smartwatch is a wrist watch with an extended functionality.

The smartwatch can be designed an independent mobile device. The smartwatch in this case can comprise the same functions as the mobile device described above.

The smartwatch can moreover also be an additional device which is dependent on a mobile device such a smart phone or another electronic device (main device) and which cannot implement its complete functionality until together with the associated electronic main device.

An additional device such as a smartwatch can basically be connected between the mobile device and the hand-held device.

The functional units can moreover comprise:
  a charging device for the connect-free charging of the hand-held device for body care, wherein a charging device comprises a data transmission module for the preferably bidirectional, wireless data transmission between the data transmission module of the hand-held device and the data transmission module of the charging device.

The functional unit can moreover be characterised in that
  the transceiver of the electronic mobile device is designed for the preferably bidirectional, wireless data transmission between the charging device and the mobile device, and
  the data transmission module of the charging device is designed for the preferably bidirectional, wireless data transmission between the mobile device and the charging device.

The data transmission module of the charging device can be constructed as the data transmission module which is described in the context of the hand-held device, and transmit the same information as the mobile device to the hand-held device. The description concerning the data transmission module further above is referred to in this context.

The charging device can e.g. apply induction coils for data transmission. These can exchange information with the hand-held device and/or with the mobile device.

The mobile device or the hand-held device can for example be designed to transfer control commands or charging parameters for the control of the charging procedure, to the charging device in a wireless manner. Thus for example settings can be made by mobile device, such that charging device starts the charging procedure on reaching a lower limit value of the charging status of the energy cell or secondary cell. Moreover, the mobile device can be set for example such that the mobile device finishes the charging procedure on reaching an upper limit value of the charging status of the energy cell.

The sporadic full charging of the energy cell or the secondary cell can thus be programmed via the mobile device for example.

Thus for example charging parameters can be transferred directly from the mobile device to the charging device or from the mobile device via the hand-held device to the charging device, thanks to a suitable design of the hardware and/or of the software in the individual devices.

The charging data, for example when, for how long was charged and also the respective technical condition of the energy cell and the charged status of the energy cell can likewise be transmitted to the mobile device, e.g. for analysis, thanks to the bidirectional communication. The evaluation of this data however can be reserved for the manufacturer.

The charging device can communicate bidirectionally with the mobile device in the same manner as the mobile device with the hand-held device. The bidirectional communication can likewise be designed with different technologies, depending on the direction.

The charging device can also be designed for unidirectional communication, with which the charging device merely receives (control) data. Thus the charging device can thus comprise a receiver with an antenna, but no transmitter.

The charging device can also be designed for unidirectional or bidirectional communication with the hand-held device. In such a constellation, the relationship amongst the devices of the functional unit must be matched. This means that in the simple relation between the hand-held device and the mobile device, the mobile device is the energy provider and thus manages the hand-held device.

In the case that the charging device is a further part of the functional unit, this unit must be adapted.

Variant 1: Communication between the hand-held device and the charging device is possible, means that the charging device must be the energy provider in the above context. This is the case inasmuch as the same data transmission module for the communication between the hand-held device and the mobile device as also between the hand-held device and the charging device is used in the hand-held device.

Variant 2: Communication between the hand-held device and the charging device is possible, means that a data transmission module which itself can be the energy provider is integrated in the hand-held device. In this case, the data transmission module in the charging device can be a passive element.

Thus for example the energy management concerning the charging of the secondary cell by the charging device can be controlled via the hand-held device. Moreover, status displays on the charging device can be effected via the hand-held device. Status displays can be effected via an LED display on the charging device, and this display indicates the functional status, such as e.g. charging or stand-by or discharging, by way of different colours. The display of the charged status can moreover also be effected by way of one or more LEDs via the hand-held device.

The functional unit according to the invention has the advantage that the hand-held device which as a rule should be as inexpensive as possible in production comprises no expensive electronics components. Thus for example the components for the wireless communication are inexpensive standard products from large-scale manufacture. The comparatively expensive electronics in contrast are available in the mentioned mobile devices as standard.

The evaluation and representation of data above all takes place on the mobile device which already comprises the expensive electronics components which are necessary for this, such as display or high-performance processor as well as an operating system for carrying out software applications or a large data memory with short access times.

Simple evaluation of data can also be carried out in the device processor of the hand-held device. This e.g. can be the computation of average values or of maximal and minimal values.

According to the invention, an existing mobile device which the user is already in possession of, as a result can be used for carrying out various functions in combination with a hand-held device for body care. The hand-held device for this merely needs to be equipped with electronic components for communication with the mobile device. The mobile device in turn is already equipped as standard with the previously mentioned electronic components for the wireless communication with the hand-held device, in particular with an active transmitting and receiving unit, such as NFC module which is to say NFC technology. A retrofitting of the mobile device as far as this is concerned as a rule is therefore not necessary.

The mobile device can also be supplemented with additional means for implementing the communication. E.g. these means can have wireless means in the case that the mobile device does not have such means as standard. The mobile device and the additional means then in turn form a unit.

The hand-held device for body care according to the invention now permits a multitude of functionalities on interaction with a mobile device. Thereby, the software application on the mobile device can be designed for the upload and download of data onto the hand-held device, as well as for the analysis and processing of the data.

Thus for example owner information, such as the name of the owner or his contact data such as resident address, email or mobile phone number can be acquired via the mobile device and stored in the mobile device and/or in the hand-held device and be called up again from this.

User information can also be acquired via the mobile device and stored in the mobile device and/or in the hand-held device. The user information can for example include the name of the user, his contact data, such as resident address, e-mail or mobile phone number. The user information can moreover include the sex, or the age.

Further data which is user-specific can moreover be acquired by the mobile device and stored on this or on the hand-held device. This data for example can be medical details. Thus data on the conditions of the gums (sensitive gums, receding of the gum), on the teeth (exposed tooth necks, fillings, implants etc.) can be acquired. Details on living habits such as eating habits, or details on applied care products such as toothpaste, mouthwash, skin cream, shaving foam etc. can moreover be acquired. This acquisition can be effected for example via an electronic questionnaire.

Data concerning the skin characteristics or the skin type or operating parameters which are derived therefrom and is on the mobile device can be stored onto the hand-held device in the case that the hand-held device is a facial care device or a body care device. The data concerning the skin characteristics for example can be derived via the analysis of photography taken in particular by the mobile device or third device (e.g. external camera). The skin characteristics can be the skin type, acne condition, pigmentation of the skin, e.g. dark or light skin, freckles and/or the humidity of the skin.

Moreover, guarantee data such as location of manufacture, time of manufacture, product batch, traceability or processor ID can be stored on the mobile device and/or the hand-held device and be called up via the mobile device.

Moreover, data for determining habits of use can be acquired by the hand-held device. The habits of use are e.g. derived by the mobile device from the recorded data by way of suitable software application. The use habits e.g. can be when the hand-held device was used (date, time of day), the duration of use or the selected body care program, e.g. the application speed of the body care element. The number and duration of usages in a certain time period can further be applied for evaluations. The evaluation of sensor data, such as e.g. the pressing pressure of the body care element upon the body surface to be treated, the zone covering, the movement course or the temperature of the body care element also belongs to this.

Data which is relevant to the maintenance and the upkeep of the hand-held device can also be acquired with the hand-held device. Maintenance data such as e.g. the exchange of a care part or care head, exchange of the energy cell, cleaning intervals or maintenance intervals for the hand-held device can be determined from this data via the mobile device by way of a suitable software application.

The point in time for the exchange of the body care element or of the care part, such as e.g. the brush head or of the razor blade can be determined for example on the basis of the number of usages or the total duration of use, on the basis of the time which has passed since the last exchange, and, as the case may be, on the basis of further influencing variables which are of relevance concerning the wear, such as pressing pressure, and this point in time can be displayed.

The duration of use of the care part however can be fixed by the user himself. Thus the user can input the desired duration of use via the software application. The user is reminded of the exchange via the software application, after completion of the defined duration of use.

The care part itself can also have a communication means such as an NFC tag, RFIF tag. The body care part or the body care element can moreover comprise an opto-electronically readable code such as bar code, line code or QR code.

The opto-electronically readable code comprises data concerning the body care part or the body care element. This data can be: technical details concerning the body care part or body care element, suitable body care programs or body care parameters concerning the body care part or body care element. The data can also only be information for the identification of the body care part or body care element. The mobile device by way of this information can then call up further data such as technical specifications or suitable body care programs or body care parameters for the identified body care part or body care element, from an internal or external data bank, for example via a mobile radio connection which e.g. creates an internet connection.

The mobile device can moreover detect the first usage of the body care part via the opto-electronically readable code (by way of NFC or camera) and can indicate the exchange to the user on exceeding the service life of the care part. This can be useful if the same hand-held device is used by several users or if a user applies several body care parts Moreover, a so-called "reset function" can be provided, which permits the user to reset the usage duration to an initial value, so that the duration of use is computed afresh.

The display is preferably effected in the software application, but despite this, a display on the hand-held device is not ruled out. The respective information can be transmitted beforehand from the mobile device to the hand-held device for the purpose of the display. It is possible to display displays on the hand-held device and mobile device, concerning certain functions, parameters or threshold values, by way of different means on both devices.

Moreover, additional information can be displayed to the user via the software application, e.g. the weather at the location of the mobile device, the current stock market values or the latest news.

The hand-held device according to the invention or the mobile device can also comprise means, in particular sensor means for determining the geographic position. This e.g. can be a GPS receiver. These means permit the detection of the current position as well as the evaluation of the covered path of the hand-held device as the case may be. Device settings for example, which are specific to the geographic region or user group of this region, in which the hand-held device is used, can be carried out by way of the information which is obtained from this.

Thus for example, with a facial care device or a body care device, the skin type can be evaluated on account of the geographic region (Africa, Europe, Asia) and be set as the case may be.

Preferably, the geographic position is determined via the mobile device, to which the hand-held device is coupled. Mobile devices as a rule comprise corresponding means as standard, via which the geographical position can be determined.

Moreover, different body care programs, e.g. cleaning programs can also be acquired or created via the mobile device. Moreover, existing body care programs can also be changed via the mobile device.

Thus e.g. certain parameters can be selected in defined regions or from a value specification, in order to personally configure the hand-held device. Furthermore, it is possible to load certain standard programs. Moreover, it is possible via the mobile device to reset the hand-held device to standard settings.

Moreover, one can further envisage calling up different body care programs or different body care parameters for different body care zones. This function can be coupled to a zone timer.

With a facial care device for example, different body care programs or different body care parameters can be applied for the face: cheeks, chin or forehead. Such care parameters for example can be the intensity of vibrations of the care head or also the duration of the treatment.

With a body care device, different body care programs or different body care parameters can be applied for example for the back, feet, hands or buttocks.

The change of the body care program or the body care parameters in particular are coupled to the zone change. The display of such a change can be effected via a mechanical (e.g. stronger vibration or no vibration), acoustic or optical signal.

The course of the different body zones which is to say the sequence of the treatment can be individually set or be deduced from a standard suggestion.

One can also envisage the change of the body care program or body care parameters for different care zones being carried out manually.

Body care programs for example comprise control-relevant data for carrying out a body care function. The body care programs for example can comprise control information with regard to the application speed of the body care element, a limit value for the pressing pressure or a movement pattern of the body care element, in particular of a brush head.

The body care program can moreover also comprise control information with regard to the care duration, in particular the cleaning duration.

The body care programs can moreover also be created or changed which is to say adapted, on account of user information. Thus for example the limit value for the maximal pressing pressure of the brush head, the movement pattern or the cleaning speed in the cleaning program can be adapted accordingly in the case of sensitive tooth necks.

The pressing pressure can be defined as a parameter. Thus a value which is seen as a maximal value for the pressing pressure of the device against its treatment surface and on exceeding which a notification is effected on the hand-held device, e.g. visually or optically, can be defined. Standard values can be set by the manufacturer. These are based its knowledge which is obtained e.g. from tests or experience. It is also conceivable for the user himself to be able to fix personal parameters via the mobile device. The parameter region varies e.g. between 100 gram to 1000 gram. The standard which is set by the manufacturer also lies in this range for example.

With regard to an oral irrigator for example, the water pressure, the water temperature, and/or the admixture of additional substances can be programmed or controlled via the mobile device. In particular, corresponding care programs which encompass values for the water pressure, the water temperature and/or additional substances can be changed or created via the mobile device.

Operating parameters for the disinfection of the hand-held device or of the care part in a disinfection unit can also be transferred via the mobile device. The parameters e.g. can be the duration and/or intensity of a UV radiation.

The application speed of the body care element can be controlled in different manner. For example, it can be controlled via the motor speed, i.e. the speed of the motor shaft. The application speed can moreover also be controlled via the control of gear stages and/or transmissions.

If the application speed is controlled via the motor speed, then the motor speed can be derived in different manners. E.g., it can be derived directly via the speed of the motor. The motor speed however can however also be derived indirectly via the application speed of the body care element, e.g. via the rotation speed at the care head.

Thus the effective motor speed can be specified to the mobile device with the direct method. Moreover, one can specify in percent as to how much the motor speed should be, on a scale from 0% to 100%. Thereby, 100% corresponds to the maximal value of the motor speed.

With the indirect method, the movement of the care head is parameterised and is calculated back to the motor speed. Thus the effective application speed of the body care element, i.e. the rotation speed at the brush head can be specified to the mobile device, from which the mobile device computes the corresponding motor speed. Moreover, one can specify how much the application speed should be in percent, on a scale from 0% to 100%. Thereby, 100% corresponds to the maximal value of the application speed. The motor speed is then derived from the application speed.

Basically, with both methods it is possible for the manufacturer to specify standard values or for the user to be able to acquire personal values. Moreover, it is possible to adapt the motor speed on account of defined body care programs. Thus the motor speed would tend to lie in lower region in the case of a soft/sensitive program.

If the hand-held device is an electrical toothbrush, then the cleaning program can moreover be directed to the individual zones of a set of teeth, for example to quadrants of a set of teeth.

A zone timer, i.e. an interval timer, for example controls the cleaning duration per zone, e.g. quadrant, as well as the pauses when changing between two zones, e.g. quadrants. The control data for the zone timer, i.e. interval timer are e.g. contained in the cleaning program. Thereby, it is also possible to define the zone sequence. Moreover, it is also possible in each case to use a cleaning program which is adapted to the individual zone.

With hand-held devices which are toothbrushes, between 1 and 14 zones, preferably between 1 and 8 zones or time intervals are defined for example. The total time which is defined for cleaning all zones (sum of the individual zone times) is between 1.5 minutes and 3.5 minutes, preferably between 2 minutes and 3 minutes. The time which is available for the individual zone is preferably between 10 seconds and 180 seconds. The mentioned numbers are preferably predefined value ranges.

A zone timer can likewise be realised with hand-held devices which are facial care devices. Thereby, the zones are defined e.g. as a first cheek, second cheek and forehead (3 zones). A different zone definition is likewise possible. The duration of the application per zone can be individually set analogously to the toothbrush. Moreover, an individual massage program can be assigned to each zone or to individual zones. Further zones on the body can likewise be defined, apart from the face zones.

With hand-held devices which are facial care devices, e.g. between 1 and 8 zones, preferably between 1 and 5 zones or time intervals are defined. The total time which is defined for the treatment of all zones (sum of the individual zone times) is between 0.5 minutes and 3 minutes, preferably between 1 minute and 2 minutes. The time which is available for the individual zone is preferably between 10 seconds and 180 seconds. The mentioned numbers are preferably predefined value ranges.

A zone timer which is not directly matched to the quadrants on cleaning teeth or to the three zones with the facial care can likewise be integrated into the software application, on the mobile device.

By way of interruptions in the body care procedure (motor stops or change of the motor speed) one can e.g. display when the next treatment position, in particular cleaning position or the next region to be treated or cleaned or the next zone to be treated or cleaned can be dealt with. The user for example can specify for how long the timer is to run in total, how many interruptions it should have, i.e. how many zones he would like to have signalised separately and how long the respective interruption should be.

A clever interaction between the mobile device and the hand-held device can also be effected. The user can move the hand-held device to the predefined zone due to the fact that the zone of the set of teeth or the body zone is displayed on the mobile device. The hand-held device can then automatically adapt the device parameters (e.g. the speed) on reaching the defined zone. The reaching of the zone can be fixed without further communication or via a communication of the position of the hand-held device from the hand-held device to the mobile device.

The zone timer can be realised with all hand-held devices for body care, for example with the mentioned functions.

Moreover, a total running time can also be displayed with the zone timer. If for example no zones are specifically defined, then a total running time, after which a signal displays that the time is completed, can be defined by the definition of a zone and a running time. The times for the total running time are to be deduced from the definition of the respective zone timer.

A switch-off function (auto-off function) of the device which is set for the user can be additionally can be provided with all hand-held devices for body care, such as for example electrical toothbrushes or facial care devices.

Thereby, the hand-held device is switched off after a predefined running time. With this, one is to avoid disadvantageous effects on account of too long an application. With toothbrushes for example, the teeth or the gums can suffer if the cleaning lasts too long. With facial care devices, skin irritations can be caused if the application is too long.

The switch-off function can be fixed or modified by the mobile device for example on the basis of skin analysis, tooth analysis or gum analysis. This modification can likewise be effected for individual care zones.

If for example the result of the automatic skin analysis is the fact that a skin irritation or acne condition is present, then the switch-off function is modified in a manner such that the device is switched off earlier, in order to take care of the irritated skin.

An auto-off function furthermore entails advantages on transport of the hand-held devices. The hand-held device is automatically stopped again after a defined time by way of this function, in the case that this has been inadvertently started. The energy cell is not unnecessarily drained by way of this.

With toothbrushes, the hand-held device is switched off by way of the auto-off function e.g. after 3 minutes to 5 minutes. With facial care devices, the respective time e.g. is 0.5 minutes to 3 minutes.

The auto-off function can be coupled to the timer or be independent of this. Coupled means that the auto-off function is activated after completion of the timer or zone timer and switches off the device, but it can also be possible to design the two time switchings in an independent manner. This means that the times of the timer or zone timer can be set independently of the auto-off function. Specifically, this means that the toothbrush, depending of the fixing of the times of the zone timer can continue to run after completion of the different zone timers, until the auto-off function switches off the hand-held device.

The cleaning program can also be put together by linking together different cleaning modes. The user for example can compose different elements into a cleaning program. For example he selects the type of movement, the speed or intensity of the movement (minimal and maximal values of the movement) and the duration, for each element. The user can create a complete cleaning program which is adapted individually to him on account of this.

Cleaning modes in the mentioned context are essentially in each case a condition or a sequence of conditions of the electrical functional element. In particular, the following modes can be applied for vibrating toothbrushes or facial cleaning devices:

regular movement (single speed)—vibration always has the same intensity:
a) sensitive (slow speed);
b) normal (middle speed);
c) quick (active);
multispeed;
waved movement—vibration intensity moves sinusoidally in a defined region;
surging movement—vibration intensity increases in a given region;
stop-and-go movement—the vibration is interrupted again and again by way of idle phases.

It is possible to define to which cleaning program or to which cleaning mode one goes, for example via key functions on the hand-held device. Thus for example, it is possible to change the complete cleaning program or also to activate or deactivate certain cleaning modes in a cleaning program. Moreover, the change of a cleaning program with a changing movement to standard setting can be controlled via key functions. The standard setting for example can be a single-speed cleaning program, i.e. a cleaning program with a regular movement or also a multispeed program which is selected from different cleaning modes.

If the hand-held device comprises illumination means such as e.g. LED modules, then the application of the illumination means can be programmed via the mobile device. Thus the illumination means for example can be programmed for displaying the charged condition of the energy cell. A user-defined display for the charged status of the energy cell can be set in this manner, e.g. via the mobile device.

Thus e.g. an LED can flash red as soon as a certain energy level of the energy cell has been fallen short off. The energy level can be defined by the user.

Moreover, a setting is also possible, with which the illumination means, given a pressing pressure which is too high, i.e. on reaching or exceeding a limit value of the pressing pressure, lights with a colour which is different to when the pressing pressure lies below the limit value.

In this case too, the mobile device and/or the hand-held device serve as a display of the pressing pressure.

The illumination means on the hand-held device can basically be used for the display of an operating condition. The illumination means can moreover also be a part of an application procedure and e.g. serve as a timer or zone timer.

Different parameters of the illumination means can be applied individually or in combination with one another, for display purposes. These parameters can be: brightness, colour, flashing, flashing frequency or the duration of the flashing, i.e. for how long the flashing occurs. The duration of the individual flashing pulses can moreover also be varied.

The brightness can be set for example as a percentage from a percent range of 0 to 100%. 0% corresponds thereby to no light (quasi switched off) and 100% corresponds to maximal brightness.

The settable colours are dependent on the applied illumination mean. Thus for example it can be the case that only individual specific colours can be displayed, such as e.g. red or green. It is also possible for the colour to be displayed, to be mixed from several colours and for a multitude of colours to be able to be produced from the colour spectrum in this manner.

The illumination means can also serve as an electrical functional element. Thus the illumination means can produce UV light for disinfection or LED light for light therapy.

If the hand-held device comprises a device for feeding fluid, for example toothpaste, from a reservoir to the body care element, for example onto the brush head, then the quantity of supplied fluid can also be determined via the mobile device. Moreover, the total quantity which is consumed over a certain time duration can be detected. This data can also serve for monitoring the degree of filling of the reservoir with fluid. Accordingly, a corresponding notification or display for the change of the reservoir can be produced on the hand-held device and/or mobile device, on falling short of a certain filling level.

The key assignment for example can also be defined via the mobile device in the case that the hand-held device comprises several function keys/function switches. Thus on the mobile device, one can select as to which switch on the hand-held device serves for switching on/off or which switch serves for the program selection.

The output of acoustic signals or sequences can be controlled via the mobile device in the case that the hand-held device comprises speaker.

The hand-held device can also have its own display. The display mode on the display for example can also be set via the mobile device.

Parameters for the control of the charging process of the energy cell, in particular the secondary cell can also be inputted in the hand-held device via the mobile device which is to say produced in the mobile device and implemented in the hand-held device. Such parameters for example can determine the charged status from which the energy cell should be charged, and whether the energy cell is to be completely charged.

Threshold values for readings from sensors can moreover be defined via the mobile device, and transmitted to the hand-held device. These threshold values trigger an action on being reached or exceeded or fallen short of, during operation of the hand-held device. This action can be: a display or notification to the user or a change of the body care function, such as switching-off, reduction of the motor speed of the electromotoric drive, a change of the care program or changing to another care program.

The threshold values can e.g. be individually set by the user, so that the respective action occurs at a point in time desired by the user.

Apart from carrying out settings and transferring operating parameters and control data to the hand-held device, data can conversely be transmitted from the hand-held device to the mobile device. The data in particular can be operating data or identification data. This data e.g. can be used for statistical evaluation. The statistical evaluation in turn can be of significance for setting or for adapting operating parameters or control data, for example in order to optimise a body care function. Thereby, a body care function is adapted starting from effectively measured data, The operating data for example can include the date and the time of use, the duration of use or the applied cleaning program. Moreover, the operating data can also include readings of sensors. Such readings can e.g. be pressure values of a pressure sensor for measuring the pressing pressure of the body care element or movement values (location, speed, acceleration, position) of a movement sensor.

Operating data can also include parameters of the functional units, for example the motor speed or the speed of the motor shaft or the temperature of a heating or cooling element.

Data on the condition of the hand-held device can also be transferred. Such data for example can relate to the charged status or the technical condition of the energy cell. The charged status is necessary for the control of the charging of the energy cell or for computing a remaining running time of the energy cell on the basis of the current charged status. The technical condition of the energy cell in turn is important for assessing as to whether the energy cell must be replaced.

The energy consumption can also be monitored in this context. Accordingly, one can envisage a warning notification or warning display being produced on the mobile device and/or the hand-held device on reaching a defined energy consumption.

Moreover, e.g. position sensor data or acceleration sensor data concerning the application zones, e.g. concerning set of teeth quadrants in the case of a toothbrush, e.g. can be acquired with the respective times to be spent. One can deduce as to how long it has been cleaned and in which zone by way of this for example. The movement of the hand-held device for implementing a body care function can moreover also be optimised by way of the analysis of position sensor data.

Position sensor data can also serve for parents being able to monitor the use of the hand-held device by their children. Thus for example by way of position sensor data, one can deduce as to whether the hand-held device was also actually moved on operation and whether the body care function was also indeed applied. This information can be suitably evaluated in the software application.

If, with regard to the hand-held device for body care, it is the case of an oral irrigator or a body care device with a care fluid, such as cream or paste, then parameters or control data such as (water) jet pressure, pulse patterns for the (water) jet, or the quantity of substance to be admixed can be inputted via the mobile device. The substance e.g. can be a mouthwash or a cleaning fluid. The point in time for de-scaling the device or parts thereof can moreover also be determined via the acquisition or detection of the operating duration.

If with regard to the hand-held device for body care, it is the case of a facial care device or a body care device, then parameters or control data such as the rotation angle or vibration intensity of the massage element such as brush, as well as the running time until the stoppage of the body care function, e.g. according to the auto-off function described above, can be set via the mobile device.

The mascara applicator for example can comprise an electromotoric drive, by way of which the applicator head can be set into oscillation, vibration, and/or into rotation. The mascara applicator can additionally or alternatively comprise an electrical heater for heating the applicator head. The mascara applicator can moreover comprise an illumination means for illuminating the applicator head.

Thus parameters or control data such as heating power, cooling power, light intensity, vibration intensity or rotation speed for example at the applicator head can be detected which is to say acquired via the mobile device.

The electrical wet shaver for example can comprise an electromotoric drive, by way of which the blade head can be brought into vibration, oscillation and/or into rotation. The number of usages can be detected with this application, in order to thus compute the point in time for the exchange of the blade head.

A software application which comprises one or more of the following functionalities which to some extent have already been mentioned further above, can be implemented on the mobile device:
  acquisition of data, such as user data, user information or user profiles, which are inputted by the user via the mobile device;
  creating or modifying body care programs on account of acquired or stored data; computing control data or operating parameters for electrical functional elements of the hand-held device on account of acquired or stored data;
  computing control values, threshold values or operating parameters;
  creating a body care program for the hand-held device:
    on the basis of determined operating and/or sensor data;
    on the basis of user-defined data;
    on the basis of used body care elements;
    on the basis of body care products which are used by the hand-held device;
  calling up body care programs;
  ensuring a wireless communication between the mobile device and the hand-held device;
  operating a mechanical unit which is connected to the mobile device, e.g. with a key, for the mechanical transmission of data;
  transferring data from the mobile device to the hand-held device;
  receiving data from the hand-held device;
  transferring data from the mobile device to a charging device;
  receiving data from the charging device;
  computing control values or operating parameters for the charging device;
  evaluating operating data, in particular creating statistic evaluations;
  evaluating sensor data, in particular creating statistical evaluations,
  creating representations of statistical evaluations from operating and/or sensor data;
  analysing sensor and operating data, and from this, generating a feedback for the user, as the case may be, with suggestions for changing the care behaviour;
  data storage and data management on the mobile device;
  creating data backups;
  downloading body care programs or operational parameters/control data from the internet;
  downloading software updates from the internet;
  installing software updates for the device processor in the hand-held device;
  installing software updates for the software application;
  creating a connection to the manufacturer or a person authorised by the manufacturer, for the purpose of transferring operating data or maintenance data as well as further information and data mentioned above, as the case may be;
  plausibility testing of the data when inputting in the app, directly before the transmission to the mobile device, or of the data received by the mobile device.

Infinite combinations of the functions mentioned above are possible.

The software application can e.g. be operated on operating systems of smartphones. Known operating systems are e.g. Apple iOs, Android, MS Windows Mobile/Phone, RIM/BlackBerry OS, Symbian.

The software application can be downloaded by an online shop onto the mobile device and be installed as a so-called "APP".

It is also possible for the software application to be able to be operated on operating systems of PCs (personal computer). Such operating systems are e.g.: MS Windows 8, Linux, Mac OS X. In this context, one can envisage data being able to be exchanged between a PC and the mobile device. A PC can provide more evaluation possibilities or a more rapid evaluation due to its large screen or its high computation capability.

The software application amongst other things serves for providing the user with data on his care behaviour, such as cleaning behaviour. The software application in this manner should assist the user in carrying out the body care and for example assist him on improving body care, such as oral hygiene.

The software application should moreover also help parents monitor the care behaviour of their children in order to intervene in a correcting manner should this become necessary. Thereby, the parents e.g. can select the settings and carry out the analysis of the data.

The software application on the mobile device for example is in the position of managing the user data and operating data of different user profiles.

The software application can e.g. be designed to manage several user profiles for a single hand-held device. This for example permits the use of one or more hand-held devices by several users via a common mobile device The software application can moreover e.g. manage several body care programs for an individual user for an individual or several different hand-held devices. The user can select the desired body care program and load it onto the hand-held device via the software application.

The software application can also automatically select the associated body care program of the registered user on the basis of the identified hand-held device which is connected to the mobile device.

The software application can thus automatically recognise the respective hand-held device via a device identification on making contact and accordingly load the associated body care program for the respective user who has registered himself for example via the software application.

Several users can thus use a common hand-held device, or in each case a personal hand-held device via a common mobile device, with individual user settings or body care programs.

The software application can also carry out a type of back-up function, by way of this likewise storing the individual parameters for the operation of the hand-held device (e.g. a body care program or currently applied body care programs) which have been stored last of all in the hand-held device. These parameters or the complete body care program can be loaded onto the hand-held device again in the event of a data loss in the hand-held device.

The back-up function can be controlled automatically by the software application or be initiated in a defined and manual manner by the user.

The software application apart from user-specific parameters or body care programs can yet store further data or complete control programs, in order in the case of a data loss on the hand-held device, to load these onto the hand-held device. One can envisage the software application periodically storing the mentioned data by way of a backup function.

One can also envisage the software application being able to update reference data such as time or date, on the hand-held device. This e.g. can be necessary when the energy cell is complete discharged and the respective reference data is thereby lost.

The software application can moreover adapt the threshold values for the display of the battery condition on account of the read-out data on the usage of the device, the charging duration times and known battery conditions. With an older device, the user for example is notified by display at an earlier stage, that it must be charged again and for example that it will take longer for example to achieve complete charging. The respective adaptations are of course set be the manufacturer on account of experience and also the technical data and characteristics of the individual components.

The individual user profiles can be protected, e.g. by way of a password. Preferably, each user also has his own body care element or care part.

The respective user for example has to register at the software application before each use, so that the mobile device known which user uses the hand-held device. The software application can therefore for example load the body care program corresponding to the registered user, onto the hand-held device.

The software applications, apart from user region can also comprise a manufacturer's region. The user region is accessible to the users. The user profiles e.g. are managed here. The manufacturer's region in contrast is reserved only for the manufacturer and/or a person authorised by the manufacturer.

The software application can moreover also permit a data reset, with which all stored usage data is deleted. The data reset can e.g. concern only the user region and exclude other regions such as the manufacturer's region. Thereby, the software/parameters/control data of the hand-held device and/or of the mobile device can be selectively reset into the factory condition.

The manufacturer's region can be protected by password and thus only be accessible to the manufacturer. E.g. maintenance data or operating data and sensor data can be stored in the manufacturer's region, and this data can be used for example for assessing the guarantee provisions. Moreover, operating data and sensor data can provide the manufacturer with valuable information on the application of the devices by the users. This information for example can be the number of uses, the use duration, the cumulative usage time or the pressing pressures, to which the device was subjected. The information can for example serve for ensuring the quality or can be incorporated into the product development.

The software application for example is designed to transfer operating data and/or sensor data or location data to the manufacturer or to a person authorised by the manufacturer, via a communication network. The data for example can be transferred automatically, i.e. without any action on the part of the user.

The manufacturer or a person authorised by this can analyse the data and upload body care programs which are changed on the basis of this, or changed operating parameters/control data, onto the mobile device.

The manufacturer or the authorised person can also upload country-specific configurations on account of the transferred location data. This can be effected for example on account of the determined GPS position or the determined place at the point on time of registering on the mobile device.

The software application can moreover comprise a professional region, to which specialists for example, e.g. dermatologists, dentists or dental hygiene specialists in the case of electrical toothbrushes, have access. This region can likewise be protected by password. Thus operating and sensor data can likewise be provided in the professional region, which these can download onto their own electronic device, e.g. in a contact-free manner, for a further evaluation. Specialists can give the users information and tips concerning improved body care on account of the data which is read out.

The specialist concerned can examine the body care such as dental care of the customer and carry out a consultation on the basis of this. The specialist if necessary can change the settings of the hand-held device for improving the health, such as dental or oral health of the user.

The software application can also be designed such that the marketer or manufacturer or a person authorised by them or a specialist can provide the user with information by way of the software application. Such information can be: promotions or advertising, product news, personally tailored advertising, adaptation of the user handbook or of the terms and conditions. Moreover, specific product recommendations for special care products, such as toothpaste, mouthwash, dental floss, interdental care devices, creams, cleaning products, etc. can given to the user on the basis of the evaluation of user data, skin analysis, tooth analysis or gum analysis.

The software application can also cooperate with so-called push services, by way of which the manufacturer or a person authorised by this or a professional can send targeted notifications to the user.

Moreover, software updates for the processors in the hand-held device as well as for the software application itself can be downloaded and installed via the mobile device. Software updates for the software application can e.g. comprise new body care programs or new functionalities, such as e.g. new tools for the statistical evaluation of the data.

The mentioned password protection, as described can limit the access for the individual user groups such as manufacturer, specialists or users, to certain regions. The individual user groups obtain a limited access on account of this, so that these cannot look into all regions Moreover, with regard to access rights, one can differentiate between write rights and read rights. However, the complete application can also be protected by a uniform password access, so that all user groups receive the same access rights via access protected by password.

The password protection does not need to be limited to the software application in the mobile device, but it can also be coupled to the access to the device processor or the microcontroller of the data transmission module in the hand-held device which can likewise be protected from access by a password.

The communication between the manufacturer and professionals and the mobile device can be effected via the internet or a mobile radio connection.

The software updates can be effected from the internet, e.g. via a website. The website can e.g. be called up by the mobile device via an opto-electronic code, for example QR code. This opto-electronic code can e.g. be attached to advertising material, on toothbrushes, on toothpaste tubes, etc.

For example, it can be the case that certain cleaning programs can only be downloaded when applying certain body care elements or care products, such as toothpastes, skin creams, mouthwash, etc. For example, it is possible for the cleaning program/cleaning parameters to only able to be downloaded via the optoelectronic code, via a suitable tag or via a web link with log-in code of the respective care part or care product.

On the other hand, the body care part can be recognised by the mobile device. This is effected for example by way of reading out an NFC Tag, RFID tag, or an opto-electronic code such as QR code, on the body care part by way of camera. The care part recognition can also be effected by way of user input. Care products which are specific to care part and are from the assortment of the manufacturer/marketer can be recommended on the mobile device by way of this.

The software applications can also be designed to carry out a tooth analysis or gum analysis (plaque or paradontois) or a skin analysis, based on photographic images, e.g. of the teeth or the skin. The results of the analysis can be taken into account on creating or adapting body care programs. The mobile device can be applied for creating the respective photographic images in the case that these devices comprise cameras.

Generally, the functions of different sensor means which are installed in the mobile device as standard, such as camera, location localisation means, microphone, pulse meter, blood pressure meter, time meter or thermometer can be used to supplement the user profile and/or to provide the user with specific assistance or advice when using the hand-held device. With this assistance, one accesses operating data and/or the user profile and suggestions for use which are adapted to the user which is to say are tailored to the user are given.

Thus film recordings or picture recordings for the purpose of analysis or evaluation of the location to be treated are taken by way of the camera of the mobile device. The analysis is effected via suitable software algorithms Suitable body care parameters or body care programs can be determined on the basis of the analysis or evaluation of the picture data or video data. These parameters or programs can be suggested to the user via the mobile device. It is also possible for the body care parameters or body care programs to be transmitted directly from the mobile device onto the hand-held device and implemented.

It is also conceivable for body care hints or other types of information to be communicated to the user via the mobile device, on the basis of the analysis or evaluation of the picture or video data. Body care hints for example can comprise specific body care instructions.

Other types of information for example can be the recommendation to seek a professional, such as doctor (dermatologist, dentist) or dental hygienist. Further information for example can also be information on the nature or the condition of the body location to be treated. The information can e.g. comprise ascertained symptoms of disease or anomalies.

The software algorithms can be part of the software application on the mobile device. The evaluation is accordingly effected by way of the mobile device.

The software algorithms however can also be a part of a software application which is installed on a third device. In this case, the picture recordings can be transferred via the mobile device to the third device by way of a mobile radio connection which e.g. creates a connection to the internet. The mobile device can receive the evaluation data or the body care parameters, body care programs or body care instructions, which are derived from this evaluation data, via the mobile radio connection.

The body locations which are to be treated for example are skin portions, teeth or gums.

The camera e.g. can be controlled via the software application. The software application thereby ensures a suitable lighting which permits an optimal analysis of the film or picture data.

The camera of a third device can also be applied for creating film or picture recordings for the purposes mentioned above. This variant has the advantage that the technical specification of the camera can be designed for a special use, so that optimal film or picture recordings can be made.

The third device with a camera can be located for example at the sales/advice location, at the doctor or specialist, where the film or picture recordings are carried out by trained professionals. The analysis of the film or picture recordings can likewise be effected on location. The optimal body care program or the optical body care parameters can likewise be computed on location on the basis of the analysis, and loaded onto the hand-held device or onto the hand-held device and/or mobile device.

According to a further variant, the hand-held device itself can comprise a camera for creating film or picture recordings for the purposes mentioned above. The camera can e.g. be arranged in the care head or in the grip body of the hand-held device. The film or picture data can be transmitted to the mobile device. The evaluation can likewise be effected via a software application on the mobile device.

Software algorithms for evaluating the film or picture recordings can also be installed on the mobile device. The software algorithms can be integrated into the software application.

The film or picture recordings for analysis however can also be sent via the software application to an external analysis device comprising suitable software algorithms. The analysis results in turn can be transferred to the mobile device.

The skin analysis can e.g. include the skin texture, skin blemishes, skin pores, skin colour and brightness of the skin. One can therefore deduce as to whether the skin is dry or well moisturised, or whether skin disorders such as acne or eczema are present.

The gum analysis can e.g. include as to whether paradonosis or receding gums are present.

The tooth analysis can e.g. include a plaque analysis.

Body care parameters which are adapted on account of the film or picture analysis can be: motor speed, rotation angle of the care head, duration of the time intervals of the zone timer or the pressing pressure and/or recommendation of specific care products in combination with the programs or parameters of the hand-held device.

Moreover, the body care program which is adapted due to the film or picture analysis can also encompass an additional function such as light treatment, treatment with electrical current or heat treatment or cold treatment.

Moreover, threshold values for body care parameters or switch-off functions can be reset on account of the film or picture analysis. Threshold values means that these values cannot be exceeded or fallen short of.

The film or picture analysis which is mentioned above can be carried out for individual care zones, e.g. forehead, cheek, chin. The changes of the body care programs on account of such a film or picture analysis in particular can be designed for individual care zones.

The changes of body care programs or of body care parameters on account of such a film or picture analysis can be submitted to the respective user as a suggestion, so that he can still always decide himself as to whether he will follow the recommendation.

The body care device can be designed such that the programming can only be carried out by a specialist and otherwise no programming by the user himself is possible. Thereby, the configuration can take place in the manner as is described at the sales point.

An electronic clock in the hand-held device can moreover be synchronised with an electronic clock installed on the mobile device, by way of the software application. The microcontroller of the data processing module can share the clock function with the device processor. The microcontroller of the data processing module e.g. makes the clock function ready in the hand-held device and provides with stored usage data with the corresponding time and the corresponding date of use.

The software application can also comprise a consultation function. The consultation function e.g. is designed to submit suggestions with regard to any care measures (health tips), in particular such as body care programs, care element type, frequency and point in time of care measures or with regard to the care products to be applied, such as toothpaste, mouthwashes or skin cream, on account of the analyses of operating data, sensor data and/or photographic images. Any recommendation, but also advertising can be coupled directly to the user profile.

The consultation function can further be coupled to the location evaluation means, e.g. a GPS signal, and the software application can display on the mobile device, as to where this product can be bought in the vicinity.

Moreover, one can specify via the software application as to when the care element, e.g. the brush head is to be exchanged. In this context, a recommendation for the purchase of a certain product and, as the case may be, the next local purchasing possibility can be given. The usage counter for the brush can be reset to "0" or "new" at this point in time in the software application, so that the counting begins afresh and the next notification for an exchange of brush is generated at the correct point in time.

Further conditions which request an action of the user, e.g. in order to continue to carry out the function in a perfect manner can be determined via the software application in cooperation with the hand-held device. This with oral irrigators e.g. can be a notification to descale.

With toothbrushes which are operated with a secondary cell, this can be a notification for the optimal charging or for improving the service life of the secondary cell. This for example can be linked to the technical condition of the energy cell.

A notification for the exchange of the primary cells can be effected with toothbrushes which are operated with primary cells. The notification e.g. can comprise the energy reserve in % detail or the residual running time of the hand-held device. The replacement of the primary cells can be provided at the correct point in time in this manner.

The design variants which have been described above are exemplary. Within the framework of the invention, the individual fashioning and elements of these design variants can be combined with other design variants without departing from the essence of this invention.

The acquisition and evaluation of operating data and sensor data permits an optimisation of the body care. The same applies to the acquisition of user-defined settings. With an electric toothbrush for example, e.g. an improved tooth cleaning or a gentle tooth cleaning can be the optimised body care.

Basically, the hand-held device according to the invention or the functional unit according to the invention permits an individualised operation of the hand-held device, which for example is directed to the wishes of the user, to user-specific characteristics, such a sex, age weight, health condition as well as habits of the user.

The hand-held device or functional unit according to the invention also permits the individualised operation of the hand-held device for several users. Thus for example individual user profiles with the respective individual operationally relevant data can be installed in the mobile device for several users who use the same hand-held device.

When loading the data from the hand-held device onto the mobile device, the usage data for example is deleted from the memory of the hand-held device, since the storage capacity is limited.

The hand-held device can be programmed such that by way of light signals for example, it indicates that the device is to be synchronised with the software application, e.g. when the memory of the hand-held device is full. If one does not read out despite the full memory, then the oldest data is overwritten, so that the protocolling can continue to be effected.

The control data and operating data can be stored in different backups via the software application. For example, a data back-up can also be carried out on connecting the software application to a PC. The data can then be stored by way of cloud computing in a "data cloud".

The software application can also comprise an electronic user handbook, from which one can obtain user information, e.g. by way of scrolling or via a search function. The software application or the electronic user handbook can also comprise videos or video instructions. The electronic user handbook can also comprise links to video instructions which can be called up via the internet.

The software application can also be provided with an export function for the back-up and further reaching analysis of the control data, operating data and user data. In this manner, the data can be exported, e.g. in a known standard format, such as CSV file. With this, the data in turn can be read into another mobile device or hand-held device.

The software application can also be coupled to common social media platforms such as Facebook. The personal cleaning of one's teeth for example can be shared with other participants. Different user data, such as cleaning duration can be compared to one another. Moreover, one can display who has cleaned their teeth at which location and time.

Feedback functions and question functions can also be integrated in the software application, and these functions permit the user for example to get in contact with the manufacturer or specialists (professionals). This is a further interaction possibility for the improvement of the personal usage habits.

The successful build-up of a connection between the mobile device and the hand-held device can be perceivably confirmed for the user at one or at both devices. A confirmation in visual form, e.g. by an illumination means, in acoustic form, e.g. by way of a noise, functionally, e.g. by starting up the motor, in a tactile form or by a combination thereof these is particularly possible.

Moreover, it is also possible for the hand-held device to be programmable by way of inputting a switch combination via an external device, e.g. in wireless manner, or mechanically. The hand-held device for example can thus be programmable via the on/off switch. A switch combination can e.g. defined via the number of actuations (pressing) of a switch and the time intervals between the pressings of the switches. A switch combination can also be defined via a combination of alternating actuation (pressing) of several switches.

The external device can be a device which is additional to the mobile device or be a mobile device itself.

Thus device configurations, in particular body care programs or user profiles can be downloaded from the external device by way of specific switch combinations, or be programmed onto the device directly via the switch by way of the corresponding switch combination.

One the other hand, one can also envisage body care programs or user profiles being downloaded from the hand-held device onto an external device, by way of specific key combinations.

One can also envisage several body care programs or body care parameters already being stored on the hand-held device at the factory, and a specific body care program or specific body care parameter being activated via a switch combination.

One can also envisage body care parameters being able to be changed via a switch combination on the hand-held device.

The hand-held device can thus be programmed independently of the software application, i.e. the respective body care programmed can be loaded onto the hand-held device or activated, independently of the software application.

The software application on the mobile device can thereby guide the user through the programming. Thereby, the succession/sequence of actuation of the on/off switch and of non-actuation with respective temporal interruptions can be shown in the software application and the user repeats the displayed procedure with the on/off switch. The software application guides the user through the programming as a guide.

Thus for example body care programs or user profiles can be loaded onto the hand-held device via the type of programming described above, at the sales location.

The software application can moreover be designed to carry out plausibility tests of the data. This can be accomplished in different steps:
1. On inputting user-specific data (e.g. name or function choice).
2. Before transferring data from the hand-held device to the mobile device
3. On receiving the data from the mobile device on the hand-held device One should avoid "false" or incorrect data being shifted and thus causing a program crash or for example blocking the hand-held device or the software application, such that these can no longer be used at that moment.

A correction program can likewise be added to the test, so that the data can be corrected and subsequently used despite this. This can be initiated in an automatic or manual manner, so that either the user himself must intervene and remedy the problem or that this occurs automatically in the background and the user has nothing to do with it.

The correction can proceed such that the correct values are left and only incorrect values are corrected or are set to a value which for example permits a transfer but which unambiguously notes that this is a value set by the program.

Figure 2:
Figure 3:
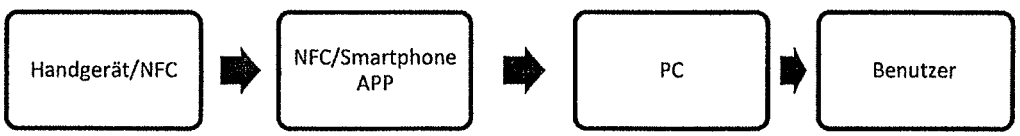
Figure 4:
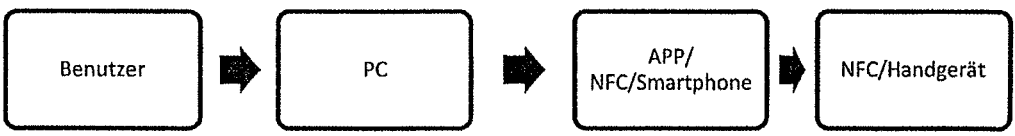

The subject-matter of the invention is hereinafter explained in more detail by way of embodiment examples which are represented in the accompanying drawings. In each case, in a schematic manner are shown in:

FIG. 1: a first communication diagram;
FIG. 2: a second communication diagram;
FIG. 3: a third communication diagram;
FIG. 4: a fourth communication diagram
FIG. 5a: an electrical toothbrush with a brush attachment part in a plan view from the upper side or front side;
FIG. 5b: an electric toothbrush with a brush attachment part in a lateral view;
FIG. 5c: an electrical toothbrush with a brush attachment part in a plan view from the lower side or rear side;
FIG. 6: an electrical toothbrush, placed onto a charging device;
FIG. 7: a charging device for an electrical toothbrush;
FIG. 8a: a push-in unit with an electronics part for an electric toothbrush according to FIGS. 5 to 6, in a lateral view;
FIG. 8b: the push-in unit according to FIG. 8a in a plan view from the upper side or front side;
FIG. 9: a part section through the electric toothbrush according to FIGS. 5 to 6;
FIG. 10: an electric wet shaver;
FIG. 11: an electrical mascara applicator;
FIG. 12: an electric facial massage device;
FIG. 13: a memory diagram;
FIG. 14a a perspective view of the rear side of a facial brush according to the invention;
FIG. 14b: a perspective view of the front side of the facial brush according to the invention and according to FIG. 14a;
FIG. 14c: a cross-sectional view of the facial brush according to the invention and according to FIGS. 14a and 14b.

Basically, the same parts are provided with the same reference numerals in the figures. The described embodiment examples are exemplary for the subject-matter of the invention and have no limiting effect. The features of individual figures where it makes sense can be combined with features of other figures.

The communication diagram according to FIG. 1 shows the data flow from the user via a mobile device, here a smartphone for example, onto the hand-held device by way of NFC transmission technology. The user e.g. carries out user-specific settings on the hand-held device via the mobile device by way of the software application which is installed on this mobile device.

The communication diagram according to FIG. 2 shows the flow of data from the hand-held device via a mobile device, here a smartphone for example, to the user by way of NFC transmission technology. Operating data and sensor data for example is transferred from the hand-held device to the mobile device. The data is evaluated for example by a software application in the mobile device and displayed to the user in the form of processed information in the software application.

The communication diagram according to FIG. 3 shows the data flow from the hand-held device via a mobile device, here a smartphone for example, to a PC. Data is transferred from the hand-held device to a smartphone by way of NFC communication technology. The mobile device is connected to a PC and transfers the data to the PC. The data transfer to the PC can also be effected in a wireless manner. The data transmission is controlled via the software application on the mobile device. The same or another software application is installed on the PC and this permits an evaluation and analysis of the data.

The communication diagram according to FIG. 4 shows the data flow from the user via a PC and a mobile device, here a smartphone of example, onto the hand-held device. User-specific data is acquired from the user at the PC via a software application installed on a PC. The data is transmitted in a wireless manner or via a temporary lead connection onto a mobile device. The same or another software application which controls the transmission of the data from the PC onto the mobile device and from the mobile device onto the hand-held device is installed on the mobile device. The data can be converted into operating parameters or control data by way of the respective software application on the PC and/or on the mobile device, before leading it further to the hand-held device. The data is transmitted from the mobile device in a wireless manner with NFC technology, onto the hand-held device by way of the software application.

FIGS. 6 and 7 by way of example show an electrical toothbrush 1 with a charging device 10. The electrical toothbrush 1 comprises a grip body 2 and a care part 3 which can be stuck onto the grip body 2 and is with a round brush head 4. A switch 5 for switching the electric toothbrush on and off is arranged in the grip body 2.

The charging device 10 can be connected via a mains cable 12 to an electricity mains. The charging device 10 comprises a stick-on pin 11, via which the electrical toothbrush 1 can be stuck onto the charging device 10.

A possible antenna in the charging device, for communication with a mobile device 21 in particular can be arranged directly behind the plane between the stick-on pin 11 and the entry point of the mains cable 12 into the housing of the charging device 10.

Figure 5A:
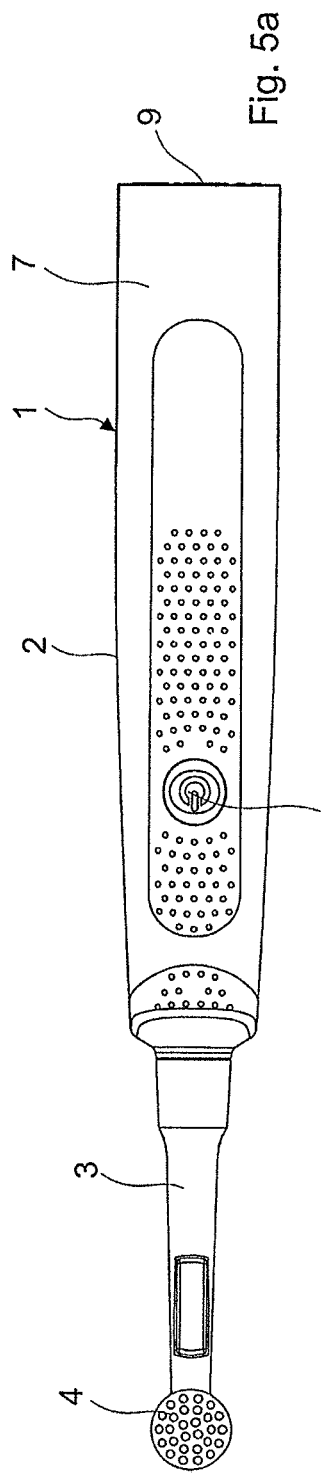
Figure 5B:
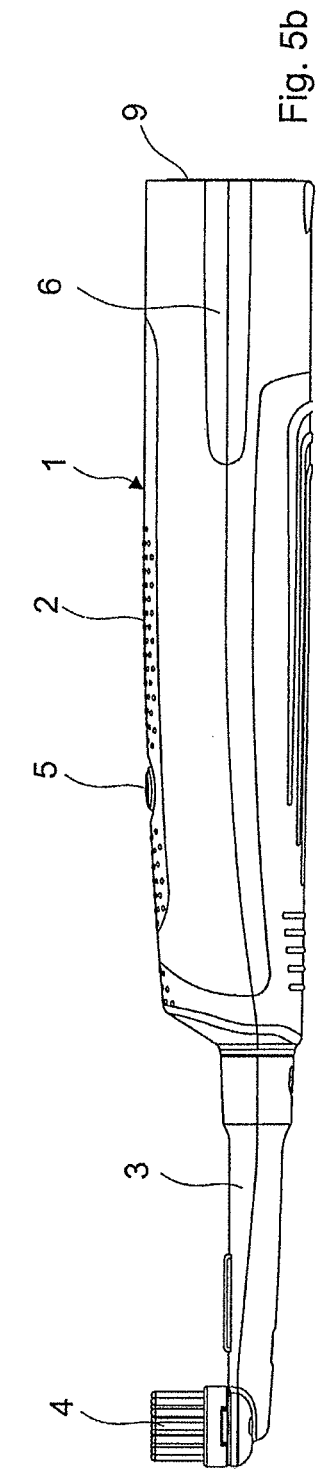
Figure 5C:
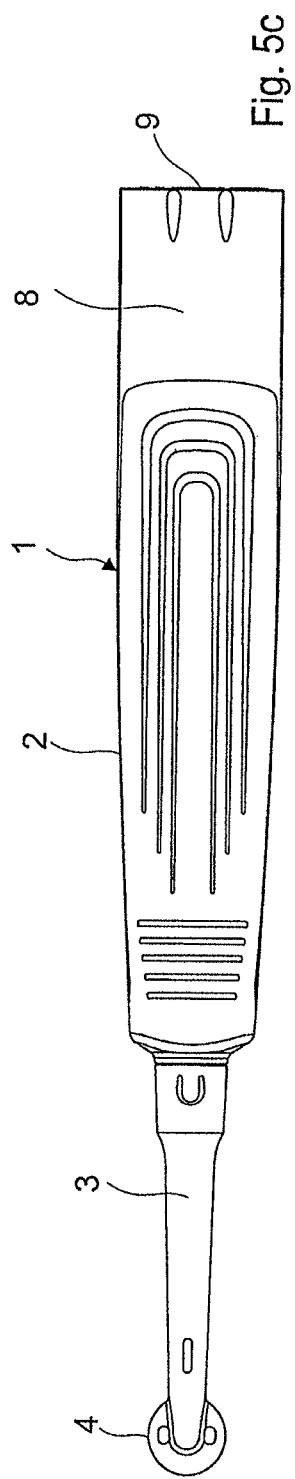

FIG. 5a shows the toothbrush 1 according to FIG. 6 from the upper side. FIG. 5b shows the toothbrush according to FIG. 6 from the side. FIG. 5c shows the toothbrush according to FIG. 6 from the lower side.

FIGS. 8a and 8b show the push-in unit 31 for the toothbrush 1 according to FIG. 6. The push-in unit 31 as is shown in FIG. 9 is pushed into the housing 39 of the grip body 2. The pushing-in is effected via a push-in opening which is arranged opposite to the care part 3, at the end of the housing 39. The push-in opening can be closed by way of a closure cover 9.

The push-in unit 31 comprises a multi-part carrier structure 32 of plastic, on which the components of the push-in unit 31 are fastened. The components of the push-in unit 31 are stuck together via elements of the carrier structure 32, into a push-in unit 31.

The carrier structure 32 is moreover not designed in a continuous manner between the two ends of the push-in unit 31. The elements of the carrier structure 32 are connected by way of known connection techniques, such as positive-fit connections (insert connections, snap connections) together with the components, into the push-in unit 31.

An energy cell 35, an electromotoric drive 36, transmission mechanics 37 and a drive shaft 33 are connected to the carrier structure 32. The care part 3 with the brush head 4 can be stuck onto the drive shaft 33.

A circuit board 38 with a device processor and with a data transmission module for the wireless transmission of data to a mobile device by way of NFC is moreover arranged on the carrier structure 32. The antenna 40 of the data transmission module is an antenna or a ferrite antenna with a ferrite core.

Moreover, an induction coil 34 for the contact-free charging of the energy cell 35 on the charging device 10 is arranged on the carrier structure 32.

The device processor on the circuit board 38 controls the electromotoric drive 36. The motor shaft of the electromotoric drive 36 and the drive shaft 33 are actively connected to one another via the transmission mechanics 37. The transmission mechanics (mechanism) 37 are designed such that a rotation movement of the motor shaft is converted into a to-and-fro movement of the drive shaft 33. The drive shaft 33 in turn interacts with movement mechanics in the care part 3 (not shown) and these mechanics convert the to-and-fro movement of the drive shaft 33 into an oscillation movement of the brush head 4.

The circuit board 38 with the data transmission module, in the assembled condition is directed to the upper side of the toothbrush and lies close to the housing wall. The mobile device 21 with its antenna is held as closely as possible to the surface of the grip body 2, so that the distance between the antenna of the mobile device 21 and the data transmission module or its antenna 40 in the grip body 2 of the toothbrush 1 is as small as possible, for transmitting data between the mobile device 21 and the toothbrush 1.

The electric hand-held device for body care with the features according to the invention, as described above, can also be present in an embodiment which is different to an electric toothbrush.

FIG. 10 e.g. shows a wet shaver 41 with electric elements. The wet shaver 41 according to the invention is designed with a data transmission module for the wireless communication with a mobile device, by way of NFC technology for example. The electrical wet shaver 41 comprises a grip body 42 as well as a blade head 43. The wet shaver 41 comprises an electromotoric drive (not shown) for producing oscillations in the blade head 43. A switch 44 for switching the wet shaver 41 on an off is provided in the grip body 42.

FIG. 11 shows an electric mascara applicator 51 which according to the invention is designed with a data transmission module for the wireless communication with a mobile device by way of NFC technology. The electrical mascara applicator 51 comprises a grip body 52 as well as an application head 53. The application head 53 can be designed as a brush. The mascara applicator 51 comprises an electromotoric drive (not shown) for producing vibrations in the application head 53. A switch 54 for switching the mascara applicator 51 on and off is provided in the grip body 52.

FIG. 12 shows an electric facial massage device 61 which according to the invention is designed with a data transmission module for the wireless communication with a mobile device by way of NFC technology. The electrical facial massage device 61 comprises a grip body 62 as well as a massage head 63. The massage head 63 comprises an electromotoric drive (not shown) for producing a rotation or vibration movement of the massage head 63. A switch 64 for switching the facial massage device 61 on and off is provided in the grip body 62.

FIG. 13 shows a data storage diagram for the hand-held device. The NFC processor (communication processor) 26 comprises two interfaces—a first interface for a communication connection to a device processor 25, as well as a second interface for a communication connection to a HF (high-frequency) part with an antenna 27. The communication via the two interfaces is effected in each case in a bidirectional manner.

Data which is now transferred from the device processor 25 to the NFC processor 26 is intermediately stored in a permanent memory which is assigned to the NFC processor 26, before this data is transmitted via the second interface to the HF part 27 and via this to a mobile device.

Vice versa, data which is received from a mobile device via the HF part 27 and is led further via the second interface to the NFC processor 26 is intermediately stored in the permanent memory, before this is transferred via the first interface to the device processor 25.

FIGS. 14a to 14c show an electric facial brush 71 which, as is described in more detail hereinafter, according to the invention, is provided with a data transmission module for the wireless communication with a mobile device by way of NFC technology.

The electric facial brush 71 comprises a grip body 72 as well as a brush head 73 which can be stuck on and is with a plurality of bristles or bristle bundles 83. The electric facial brush 71 comprises an electromotoric drive 80 which cooperates with the brush head 73 for producing a rotation and/or vibration movement in the brush head 73. Vibrations are produced via an eccentric element in the electromotoric drive 80 and are transmitted onto the brush head 73.

A switch 74 for switching the facial brush 71 on and off are provided in the grip body 72. A circuit board 75 is moreover arranged in the grip body 72. An NFC module 76 with a transmitting and receiving unit is arranged on the circuit board 75. An LED display 81 for status displays is arranged on the circuit board 75. Moreover, a secondary cell 79 as well as an induction coil 77 for charging the secondary cell 70 is arranged in the grip body 72. An antenna is furthermore also arranged in the grip body 72, but this is not explicitly represented in the present drawing. The antenna is integrated in the NFC module 76.

The circuit board 75, the secondary cell 79, the NFC module 76 and the induction coil 77 are connected via a carrier structure 78 into an assembly unit. The housing wall of the grip body 72 can be divided into two half-shells via a joining seam 84, by which means an access to the inside of the grip body 72 is created. The grip body 72 however on manufacture is closed such that it is only accessible again by way of destroying the housing.

The invention claimed is:

1. An electrical toothbrush for dental care, comprising:
   a dental care part;
   a grip body for holding the toothbrush;
   an electromotoric drive disposed in the grip body for mechanical movement of the dental care part and carrying out an electrically operated dental care function; and
   an electronics part comprising:
      a device processor that controls the electrically operated dental care function;
      an energy cell that supplies electrical energy to the device processor and the electromotoric drive; and
      a data transmission module configured to perform wireless bidirectional data transmission with an electronic mobile device using near-filed communication technology (NFC), the data transmission module comprising:
         a microcontroller;
         at least one memory for storing data; and
         an antenna disposed in the grip body,
      wherein the data transmission module is configured to obtain all of the electrical energy necessary for its operation in a contact-free manner via electromagnetic waves produced by the electronic mobile device, when the antenna is located in an influence region of the electronic mobile device, and not receive electrical energy from the energy cell.

2. The toothbrush according to claim 1, wherein the data transmission module is configured to obtain electrical energy via electromagnetic waves which are received by the antenna.

3. The toothbrush according to claim 1, wherein the data transmission module comprises a permanent memory.

4. The toothbrush according to claim 1, further comprising an electrical functional element for carrying out a further electrically operated dental care function.

5. The toothbrush according to claim 4, wherein the electrical functional element is:
   an electrical heater for heating a dental care element;
   a UV device for producing UV light for disinfection of the toothbrush or parts thereof;
   a pump for delivering a fluid; or
   an ionisation device.

6. The toothbrush according to claim 1, wherein the electromotoric drive and the antenna of the data transmission module are arranged in the grip body at a distance from one another of at least 2 cm.

7. The toothbrush according to claim 6, wherein the electromotoric drive is arranged in an upper section of the grip body which faces the dental care part, and the antenna of the data transmission module is arranged in a lower section of the grip body which is away from the dental care part.

8. The toothbrush according to claim 1, wherein the grip body comprises a housing, and the antenna of the data transmission module is:
   disposed directly on an inner side of a wall of the housing,
   disposed directly on an outer side of the wall,
   disposed between a first and second layer of the wall, or
   integrated into the wall.

9. The toothbrush according to claim 1, wherein the electronics part is configured for data from the microcontroller or data from the electronic mobile device to be stored on the memory.

10. The toothbrush according to claim 1, wherein the toothbrush is configured to transmit data onto the electronic mobile device, by way of actuating a key or a mechanical switch on the toothbrush.

11. The toothbrush according to claim 1, wherein the toothbrush is configured to communicate with the electronic mobile device using different communication means in different directions.

12. The toothbrush according to claim 1, wherein an opto-electronic code is attached on the dental care part or dental care element, and this code comprises coded information which can be read out by the electronic mobile device.

13. A functional unit comprising:

the toothbrush according to claim 1, and the electronic mobile device, wherein the electronic mobile device comprises an active transmitting and receiving unit for bidirectional wireless data transmission between the toothbrush and the electronic mobile device.

14. The functional unit according to claim 13, further comprising:

a charging device for contact-free charging of the toothbrush, the charging device comprising a data transmission module for unidirectional or bidirectional wireless data transmission between the data transmission module of the toothbrush and the data transmission module of the charging device.

15. The functional unit according to claim 14, wherein the transmitting and receiving unit of the electronic mobile device is configured for unidirectional or bidirectional wireless data transmission between the charging device and the electronic mobile device, and the data transmission module of the charging device is configured for unidirectional or bidirectional wireless data transmission between the electronic mobile device and the charging device.

16. The functional unit according to claim 13, wherein the toothbrush and the electronic mobile device are configured to communicate with one another using different communication means in different directions.

17. A method for operating the functional unit according to claim 13 by way of the electronic mobile device, wherein dental care parameters or dental care programs are transmitted wirelessly onto the toothbrush via a software application operated on the electronic mobile device.

18. The method according to claim 17, wherein operating data of the toothbrush is received wirelessly by the electronic mobile device and evaluated by the software application operated thereon.

19. The method according to claim 17, wherein sensor data of the toothbrush is received by the electronic mobile device wirelessly and evaluated by the software application which is operated thereon.

20. The method according to claim 17, wherein at least one picture recording or video recording of a dental location to be treated is created by a camera of the electronic mobile device, and the at least one picture recording or video recording is evaluated via the software application, and suitable dental care parameters or dental care programs are determined based on the evaluation and via the electronic mobile device are suggested to the user or transmitted onto the toothbrush, or dental care hints or other information is communicated to the user via the electronic mobile device.

* * * * *